(12) United States Patent
Wolfe et al.

(10) Patent No.: US 6,861,416 B2
(45) Date of Patent: Mar. 1, 2005

(54) OXAZINONES AND METHODS FOR THEIR USE AND SYNTHESIS

(75) Inventors: Saul Wolfe, North Vancouver (CA); Gennady Shustov, Edmonton (CA)

(73) Assignee: Chirologix Pharmaceuticals, Inc., North Vancouver (CA)

(*) Notice: Subject to any disclaimer, the term of this patent is extended or adjusted under 35 U.S.C. 154(b) by 0 days.

(21) Appl. No.: 10/411,547

(22) Filed: Apr. 10, 2003

(65) Prior Publication Data

US 2004/0023956 A1 Feb. 5, 2004

Related U.S. Application Data

(63) Continuation of application No. 10/210,970, filed on Aug. 2, 2002, now abandoned.
(60) Provisional application No. 60/310,103, filed on Aug. 3, 2001.

(51) Int. Cl.$^7$ .......................... A61K 31/33; A61K 31/54; C07D 265/00; C07D 273/00
(52) U.S. Cl. ..................... 514/183; 514/228.8; 544/63; 544/68
(58) Field of Search .............................. 514/183, 228.8; 544/63, 68

(56) References Cited

U.S. PATENT DOCUMENTS

| 4,013,653 A | 3/1977 | Wolfe ..................... 260/244 R |
| 4,775,670 A | 10/1988 | Sykes et al. ................. 514/210 |
| 4,822,788 A | 4/1989 | Kishimoto et al. ......... 514/210 |
| 5,552,543 A | 9/1996 | Wolfe et al. ............... 544/58.4 |
| 6,399,600 B1 | 6/2002 | Wolfe et al. ............. 514/228.8 |

FOREIGN PATENT DOCUMENTS

| JP | 62-215585 | 9/1987 |
| WO | 9207837 | * 5/1992 |

OTHER PUBLICATIONS

CVhemical Abstract DN 117:69872, also cited as WO 9207837.*
Baldwin et al. "The synthesis of potential γ–lactam antibiotics containing a cycloserine nucleus." *Tetrahedron Letters* (1990) 31(15):2211–2212.
Barlos et al. "Anwendung von N–Tritylmethionin zur Darstellung von biologisch und synthetisch interessanten Heterocyclen." *Liebigs Ann. Chem* (1988) pp. 1127–1133 (Engl. abstr.).
Bruncko et al. "N–bromoacetamide. A new nitrogen source for the catalytic asymmetric aminohydroxylation of olefins." *Angew. Chem. Int. Ed. Engl.* (1997) 36(13/14):1483–1486.
Frankel et al. "DL–Cyclocanaline (cyclohomoserine) and related compoubds." *J. Chem. Soc. Secition C: Organic Chemistry* (1969) pp. 1746–1749.

Furrow et al. "Practical Access to Highly Enantioenriched C–3 Building Blocks via Hydrolytic Kinetic Resolution." *J. Org. Chem.* (1998) 63:6776–6777.
Gao et al. "Asymmetric synthesis of both enantiomers of tomoxetine and fluoxetine. Selective reduction of 2,3–epoxycinnamyl alcohol with red–A1." *J. Org. Chem.* (1988) 53:4081–4084.
Hatayama et al. "Highly enantioselective epoxidation of 2,2–dimethylchromenes." *Synlett.* (1992) 407–409.
Hora, "Synthesis of 7–α–Acetylthio–(6'R)– 6'–Methyl–3'–Oxotetrahydro–1,1'2'–Oxazino[4',5':13β,17β]–18–Norandrost–4–En–3–One." *Collection Czechoslov. Chem. Commun.* (1967) 32:2820–2825.
Hora, "Synthesis of Steroidal Tetrahydro–1, 2–Oxazine–3–One Derivatives." *Collection Czechoslov. Chem. Commun.* (1965) 30:70–80.
Hou et al. "Desymmetric ring–opening of meso–epoxides with anilines: a simple way to chiral β–amino alcohols." *Tetrahedron: Asymmetry* (1998) 9:1747–1752.
Jacobson et al. "Highly enantioselective epoxidation catalysts derived from 1,2–diaminocyclohexane." *J. Am. Chem. Soc.* (1991) 113:7063–7064.
Karpeiskii et al. "The Mechanism of Reaction of Cycloserine and Related Compounds with Aspartate–Glutamate Transaminase." *Biokhimiya* (1963) 28(2):345–352.
Khomutov et al. "Synthesis of Cyclocanaline (Homocycloserine) and Related Compounds." *Izvestiya Akademii Nauk SSSR* (1962) 12:2161–2166 *Chemical Abstracts* 13944, 1963.
Khomutov et al. "Synthesis of Tetrahyro–1, 2–Oxazin–3–One." *Izvestiya Akademii Nauk SSSR, Otdelenie Khimicheskikh Nauk* (1962) 6:1074–1076 *Chemical Abstracts* 13754a, 1962.
Khomutov et al. "The Relationship Between Biological Activity and Chemical Properties." *Biokhimiya* (1961) 26(5): 772–781.
Khomutov, "Synthesis of O–Substituted Hydroxylamines." *Zhurnal Obshchei Khimii* (1961) 31(6):1992–1995.
Khomutov et al. "On Some Cycloserine Derivatives Possessing Antituberculose activity." *Voprosy Meditsinskoi Khimii* (1962) 8:389–391 (English abstr.).
Kotsuki et al. "High pressure–promoted uncatalyzed hydrolysis of epoxides." *Tet. Lett.* 34:4031–4034.

(List continued on next page.)

Primary Examiner—Richard L. Raymond
Assistant Examiner—Sudhaker B. Patel
(74) Attorney, Agent, or Firm—Lahive & Cockfield, LLP; Elizabeth A. Hanley, Esq.; Cynthia M. Soroos, Esq.

(57) ABSTRACT

The invention pertains, at least in part, to new intermediates and synthetic methods for the stereospecific synthesis of oxazinone compounds, which are useful, for example, as antibiotics. The invention also pertains to novel olefinic oxazinone compounds, methods for their synthesis, and methods of using these compounds for the synthesis of oxazinones. The invention also pertains to methods for using the compounds to treat bacterial associated states in subjects.

45 Claims, No Drawings

OTHER PUBLICATIONS

Kuehl et al. "Communications to the Editor: A–4–Amino–3–Isoxazolidone, A New Antibiotic." *J. Am. Chem. Soc.* (Apr./Jun. 1955) 77:2344–23450.

Linker, "The Jacobsen–Katsuki epoxidation and its controversial mechanism." *ACIEE* (1997) 36:2060–2.

Markova et al. "Hydroxylamine Derivatives." *Chemical Abstracts* 70: 66520h (1970).

Meguro et al. "Ytterbium triflate and high pressure–mediated ring opening of epoxides with amines." *J. Chem. Soc. Perkin. Trans. 1* (1994) pp. 2597–2601.

Molander et al. "Reduction of vinyloxiranes with samarium diiodide. An efficient route to functionalized chiral, nonracemic (E)–allylic alcohols." *J. Org. Chem.* (1986) 51:5259–5264.

O'Brien et al. "Sharpless asymmetric aminohydroxylation: Scope, limitations, and use in synthesis." *Angew. Chem. Int. Ed.* (1999) 38(3):326–329.

Olah et al. "Synthetic methods and rections.43. Preparation of fluorohydrins from epoxides with pyridinium poly–hydrogen fluoride." *Isr. J. Chem.* (1978) 17:148–149.

Oshima et al. "Palladium–catalyzed selective hydrogenolysis of alkenyloxiranes with formic acid. Stereoselectivity and synthetic utility." *J. Am. Chem. Soc.* (1989) 111:6280–6287.

Pfenninger, "Asymmetric epoxidation of allylic alcohols: The sharpless epoxidation." *Synthesis* (1986) pp. 89–116.

Procter et al. "β–Lactams From Tetrahydro–1,2–Oxazine–3, 6–Diones, and a Labelling Study of the Product Stereochemistry." *Tetrahedron* (1995) 51(47):12837–12842.

Rosenthal et al. "Insecticidal Properties of Some Derivatives of L–Canavanine", *J. Agric. Food Chem.* (1995) 43:2728–2734.

Sharpless et al. "On the mechanism of titanium–tartrate catalyzed asymmetric epoxidation." *Pure Appl. Chem.* (1983) 55:1823–1836.

Shimizu et al. "Highly selective ring opening of epoxides with silicon tetrafluoride: preparation of fluorohydrins." *Tett. Lett.* (1988) 29:4101–4104.

Strominger et al. "Composition of the cell wall of *staphylococcus aureus*: Its relation to the mechanism of action of penicillin," *J. Biol. Chem.* 234:3263–3268 (1959).

Tabei et al. "Reaction of β–bromoacetoacetyl bromide with N–phenylhydroxylamine derivatives: synthesis of 1,2–oxazine derivatives." *Chemical Abstracts* 92:76436 (1980).

Tabei et al. "Reaction of β–bromoacetoacetyl bromide with N–phenylhydroxylamine derivatives: Synthesis of 1,2–oxazine derivatives." *Chem. Pharm. Bull.* (1979) 27(8): 1842–6.

Tabei et al. "Organic Sulfites Containing a 1,2–Oxazine Ring." *Chem. Pharm. Bull.* (1980) 28(1): 330–336.

Tao et al. "Reversal of regioselection in the asymmetric aminohydroxylation of cinnamates." *Tet. Lett.* (1998) 39:2507–2510.

Umemoto et al. "Power and structure–variable fluorinating agents. The N–Fluoropyridinium salt system." J. Am. Chem. Soc. (1990) 112:8563–75.

Wang et al. "Catalytic asymmetric dihydroxylation of cis- –disubstituted olefins." *J. Am. Chem. Soc.* (1992) 114:7568–7570.

Wolfe et al. "1992 p–Hydration of the Carbonyl Group. A Theoretical Study of the Cooperative Mechanism." *J. Am. Chem. Soc.* (1995) 117:4240–4260.

Wolfe, "Lemieux Award lecture: Studies related to the penicillin receptor." *Canadian J. Chem.* (1994) 72: 1014–32.

Wolfe et al. "A semiempirical molecular orbital study of the methanolysis of complex azetidinones. A combined MM and QM analysis of the interaction of $\Delta^2$–and $\Delta^3$–cephems with the penicillin receptor." *Canadian J. Chem.* (1994) 72:1044–50.

Wolfe et al. "Ab initio molecular orbital calculations on the neutral hydrolysis and methanolysis of azetidinones, including catalysis by water. Relationship to the mechanism of action of β–lactam antibiotics." *Canadian J. Chem.* (1994) 72:1033–43.

Wolfe et al. "Conformation–activity relationships and the mechanism of action of penicillin." *Canadian J. Chem.* (1988) 66(11):2733–50 (English abs.).

Wolfe et al. "Interactive design and synthesis of a novel antibacterial agent." *Canadian J. Chem.* (1994) 72(4):1051–65.

Wolfe et al. "MMPEP: Development and evaluation of peptide parameters for Allinger's MMP2(85) programme, including calculations on crambin and insulin." *Canadian J. Chem.* (1988) 66(11):2687–2702.

Wolfe et al. "Phenceptin: a biomimetic model of the phenytoin receptor." *Canadian J. Chem.* (1988) 66(11):2751–62.

Wolfe et al. "Theoretical conformational analysis of peptides. Evolution of a strategy and its application to cholecystokinin analogs." *Canadian J. Chem.* (1988) 66(11):2703–14.

* cited by examiner

OXAZINONES AND METHODS FOR THEIR USE AND SYNTHESIS

RELATED APPLICATIONS

This application claims priority to U.S. Provisional Application Ser. No. 60/310,103, entitled "Intermediates and Methods For Synthesizing Oxazinones," filed Aug. 3, 2001, the entire contents of this application are hereby incorporated herein by reference. This application is related to U.S. Pat. No. 6,399,600 B1, issued on Jun. 4, 2002, the entire contents of this patent are hereby incorporated herein by reference.

BACKGROUND OF THE INVENTION

Many antibiotics act by interfering with the biosynthesis of bacterial cell walls (Strominger et al. *J. Biol. Chem.* 234:3263 (1959)). The completion of bacterial cell wall synthesis is mediated by enzymes termed penicillin-binding proteins (PBPs) which cross-link different peptidoglycan chains. In particular, PBPs link the penultimate D-Ala residue of a peptidoglycan terminating in a N-acyl-D-Ala-D-Ala moiety to the terminal amino group of a lysine residue of another peptidoglycan chain. Glycopeptide transpeptidase is an example of a PBP present in many bacteria.

Most known PBPs are serine peptidases, which have a conserved Ser-X-X-Lys sequence at the active site. The β-lactam family of antibiotics, whose members include penicillins and cephalosporins, inhibit PBPs by forming a covalent bond with the serine hydroxyl group to produce an acyl-enzyme. The enzyme is then unable to carry out the final step in the biosynthesis of the bacterial cell wall. As a result the wall is weakened, becomes permeable to water, and the bacterial cell swells, bursts, and dies.

The simplest kinetic description of the reaction between a bacterial enzyme (Enz) and a β-lactam antibiotic is given in Scheme 1 below:

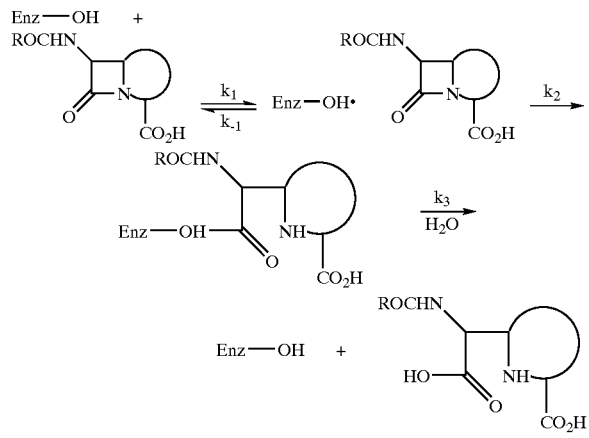

SCHEME 1

In addition to the PBP's, many bacteria also produce a second type of penicillin-recognizing enzyme, known as a β-lactamase. PBPs and β-lactamase exhibit the same kinetics as set forth in Scheme 1 above, but with different rate constants. This difference in rate constants has important consequences. In the case of PBP's, $k_2 \gg k_3$ (i.e., the formation of the acyl-enzyme is much faster than its hydrolysis). The result is that the enzyme is inhibited, and antibacterial activity may be observed. In the case of a β-lactamase, $k_2 \approx k_3$ (i.e., the formation and hydrolysis of the acyl enzyme proceed at comparable rates). These kinetics lead to regeneration of the enzyme, and inactivation of the antibiotic as a result of the net hydrolysis of the β-lactam bond in the deacylation step. The latter sequence of reactions comprises the principle mechanism of bacterial resistance to β-lactam antibiotics. Useful antibacterial activity is generally considered to require $k_2/k_1 \geq 1000 M^{-1} sec^{-1}$ and $k_3 \leq 1 \times 10^{-4} sec^{-1}$.

Resistance to antibiotics is a problem of much current concern. Alternatives to existing antibiotics are invaluable when bacteria develop immunity to these drugs or when patients are allergic (approximately 5% of the population is allergic to penicillin). Because of the relatively low cost and relative safety of the β-lactam family of antibiotics, and because many details of their mechanism of action and the mechanism of bacterial resistance are understood, one approach to the problem of resistance is to design new classes of compounds that will complex to and react with a penicillin recognizing enzyme, and be stable to the hydrolysis step. In order to be effective, the antibacterial agent should have the ability to react irreversibly with the active site serine residue of the enzyme.

The crystal structures of β-lactamases from *B. licheniformis*, *S. aureus* and *E. coli* (RTEM) suggest a chemical basis for resistance to β-lactam antibiotics. Apart from the conserved Ser-X-X-Lys active site sequence, these β-lactamases have a conserved Glu166 which participates in the hydrolysis of the acyl-enzyme. It appears that the acylated hydroxyl group of the active site serine and the carboxyl group of Glu 166, together with a water molecule, are involved in the hydrolysis step. The water molecule and the carboxyl group act in concert and this interaction is the source of bacterial resistance to β-lactam antibiotics. Drug design must therefore include a process for the removal or inactivation of this water molecule.

Numerous β-lactam compounds have been developed in the past which are structural analogues of penicillin and can complex to and react with penicillin recognizing enzymes. Like penicillin, such antibiotics are presumed to be conformationally constrained analogues of an N-acyl-D-Ala-D-Ala peptidoglycan moiety, the O=C—N β-lactam bond serving as a bioisostere of the D-Ala-D-Ala peptide bond. Effective antibacterial activity also requires a properly positioned carboxyl group or equivalent and a hydrogen bonding hydroxyl or acylamino group. A computer implemented molecular modeling technique for identifying compounds which are likely to bind to the PBP active site and, thus, are likely to exhibit antibacterial activity has been developed (U.S. Pat. No. 5,552,543).

Some oxazinones having possible biological activity are known in the prior art Khomutov et al. synthesized tetrahydro-1,2-oxazin-3-one (Chem. Abs. 13754a, 1962) and 4-benzamidotetrahydro-1,2-oxazin-3-one (Chem. Abs. 58, 13944b, 1963). The latter compound is also known as N-benzoyl-cyclocanaline. According to Khomutov, cyclocanaline is known to inhibit glutamate-aspartate transaminase and exhibits activity against tuberculosis bacilli. The structure of cyclocanaline is shown in formula (A) below.

(A)

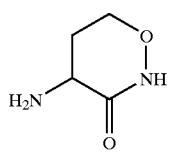

Frankel et al. reported the synthesis of DL-cyclocanaline (4-amino-tetrahydro-1,2-oxazin-3-one) hydrochloride from canaline dihydrochloride in 1969 (J. Chem. Soc. (C) 174601749, 1969) and recognized that DL-cyclocanaline is a higher homologue of the antibiotic cycloserine.

SUMMARY OF THE INVENTION

The invention pertains, at least in part, to new intermediates and synthetic methods for the stereospecific synthesis of oxazinone compounds, which are useful, for example, as antibiotics. The invention also pertains to novel olefinic oxazinone compounds, methods for their synthesis, and methods of using these compounds for the synthesis of oxazinones.

In one embodiment, the invention pertains to olefinic oxazinones of the formula (I):

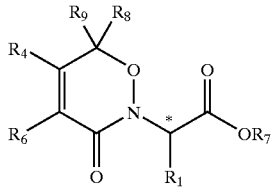

(I)

wherein:
  $R_1$ is an amino acid side chain mimicking moiety;
  $R_4$, $R_6$, $R_8$, and $R_9$ are substituting moieties;
  $R_7$ is hydrogen, a protecting moiety, or a prodrug moiety, and acceptable salts and esters thereof.

The invention also pertains, at least in part, to methods for synthesizing oxazinones of the formula (II):

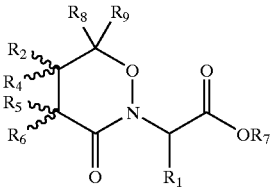

(II)

wherein:
  $R_1$ is an amino acid side chain mimicking moiety;
  $R_2$ is halogen, OH, SH, $NH_2$, $NHCOR_3$, or an electronegative moiety;
  $R_3$ is an antibacterial substituent;
  $R_4$, $R_8$ and $R_9$ are each independently selected substituting moieties;
  $R_5$ is OH, $NH_2$, $NHCOR_3$, or an electronegative moiety; and
  $R_6$ is a substituting moiety or the oxygen of a carbonyl group when taken together with $R_5$;
  $R_7$ is hydrogen, a protecting moiety, or a prodrug moiety, and pharmaceutically acceptable salts and esters thereof The method includes contacting an olefinic oxazinone of formula (I) with a derivatizing agent, under appropriate conditions such that an oxazinone of formula (II) is synthesized.

In another embodiment, the invention pertains in part to epoxide oxazinones of formulae (III) and (IV):

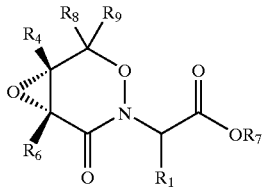

(III)

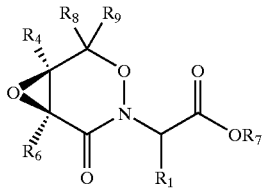

(IV)

wherein:

$R_1$ is an amino acid side chain mimicking moiety;
  $R_4$, $R_6$, $R_8$ and $R_9$ are each independently selected substituting moieties;
  $R_7$ is hydrogen, a protecting moiety, or a prodrug moiety, and acceptable salts and esters thereof.

In yet another embodiment, the invention pertains to methods for the synthesis of olefinic oxazinones. The method includes contacting a diolefin of formula (V) with a cyclization catalyst under appropriate conditions, such that an olefinic oxazinone of formula (I) is formed. The diolefin of formula (V) is:

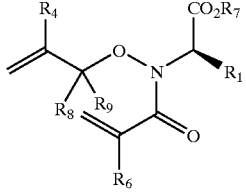

(V)

wherein:

$R_1$ is an amino acid side chain mimicking moiety;
  $R_4$, $R_6$, $R_8$ and $R_9$ are each independently selected substituting moieties;
  $R_7$ is hydrogen, a protecting moiety, or a prodrug moiety, and acceptable salts and esters thereof.

The invention also pertains, at least in part, to another method for the synthesis of an olefinic oxazinone of formula (I). The method includes treating an olefinic triphenyl phosphine salt with ozone under appropriate conditions, such that an olefinic oxazinone is formed. The olefinic triphenyl phosphine salt is of formula (VI)

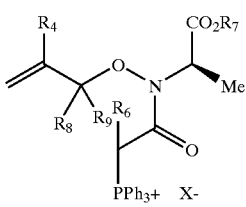

(VI)

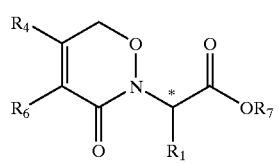

(VII)

wherein:

R₁ is an amino acid side chain mimicking moiety;

R₄, R₆, R₈ and R₉ are each independently selected substituting moieties;

R₇ is hydrogen, a protecting moiety, or a prodrug moiety, and pharmaceutically acceptable salts and esters thereof.

In another embodiment, the invention pertains to a method for treating a bacterial associated state in a subject. The method includes administering to said subject an effective amount of an oxazinone compound of the invention, e.g., a compound of formula (I), (II), (III), (IV) or otherwise described herein.

In yet another embodiment, the invention includes pharmaceutical compositions comprising an effective amount of a compound of the invention, e.g., a compound of formula (I), (II), (III), (IV) or otherwise described herein.

DETAILED DESCRIPTION OF THE INVENTION

The invention pertains, at least in part, to new intermediates and synthetic methods for the stereospecific synthesis of oxazinone compounds, which are useful, for example, as antibiotics. The invention also pertains to novel olefinic oxazinone compounds, methods for their synthesis, and methods of using these compounds for the synthesis of oxazinones.

In one embodiment, the invention pertains to an olefinic oxazinone of the formula (I):

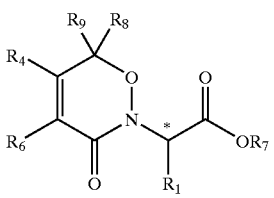

(I)

wherein:

R₁ is an amino acid side chain mimicking moiety;

R₄, R₆, R₈ and R₉ are each independently selected substituting moieties;

R₇ is hydrogen, a protecting moiety, or a prodrug moiety, and acceptable salts and esters thereof.

In a further embodiment, the olefinic oxazinones of formula (I) include olefinic oxazinones represented by formula (VII):

wherein

R₁ is an amino acid side chain mimicking moiety;

R₄ and R₆ are each independently lower alkyl or hydrogen;

R₇ is hydrogen, a protecting moiety, or a prodrug moiety, and acceptable salts and esters thereof.

The language "amino acid side chain mimicking moiety" includes moieties that are amino acid side chains or mimic amino acid side chains and which allow the oxazinone (e.g., a compound of formula II) to perform its intended function by, e.g., mimicking the structure or function of an amino acid side chain. For example, the "amino acid side chain mimicking moiety" allows the oxazinone to interact with the active site of a penicillin recognizing enzyme. Examples of amino acid side chain moieties include the side chains of natural and unnatural, D- and L-amino acids. For example, the amino acid side chain mimicking moiety may be the side chain of a neutral amino acid (e.g., alanine, valine, leucine, isoleucine, phenylalanine, tryptophan, or methionine), a polar amino acid (e.g., glycine, serine, threonine, cysteine, tyrosine, asparagine, or glutamine), or a charged amino acid (e.g., aspartic acid, glutamic acid, lysine, arginine, or histidine). In an embodiment, the amino acid side chain mimicking moiety is the side chain of alanine (e.g., methyl).

In another embodiment, the amino acid side chain mimicking moiety is substituted or unsubstituted alkyl, e.g., lower alkyl. The side chain mimicking moiety may be substituted with any substituent that allows it to perform its intended function (e.g., when present in the oxazinone, it should allow the oxazinone to interact with penicillin recognizing enzyme, etc.). Examples of alkyl amino acid side chain mimicking moieties include straight chain, branched and cyclic alkyl groups. Examples of alkyl groups include, but are not limited to, methyl, ethyl, i-propyl, n-propyl, i-butyl, n-butyl, t-butyl; pentyl, cyclopentyl, cyclohexyl, or hexyl. Other examples of amino acid side chain mimicking moieties include alkenyl, alkynyl, carbonyl, aralkyl or aryl moieties. Examples of aryl moieties include substituted and unsubstituted phenyl and substituted and unsubstituted heteroaryl.

The language "protecting moiety" includes groups which can be used to protect the carboxylic acid functionality during synthesis of the oxazinone compound. Any protecting moiety known in the art and compatible with the other functionality of the oxazinones, olefinic oxazinones, and/or epoxide oxazinones may be used. Examples of protecting moieties include esters, groups known to those of skill in the art, and those described in Greene, *Protective Groups in Organic Synthesis*, Wiley, New York (1981), incorporated herein by reference.

The language "prodrug moiety" includes moieties which can be cleaved in vivo to yield an active drug (see, e.g., R. B. Silverman, 1992, "The Organic Chemistry of Drug Design and Drug Action", Academic Press, Chp. 8). Prodrugs can be used to alter the biodistribution or the pharmacokinetics for a particular compound. Examples of prodrug moieties include substituted and unsubstituted, branched or unbranched lower alkyl moieties, lower alkenyl moieties, di-lower alkyl-amino lower-alkyl moieties (e.g., dimethylaminoethyl), acylamino lower alkyl moieties (e.g., acetoxymethyl), acyloxy lower alkyl moieties (e.g., pivaloyloxymethyl), aryl moieties (e.g., phenyl), aryl-lower alkyl (e.g., benzyl), substituted (e.g., with methyl, halo, or methoxy substituents) aryl and aryl-lower alkyl moieties, amides, lower-alkyl amides, di-lower alkyl amides, and hydroxy amides. Also included are groups which may not need to be removed to yield an active drug.

The term "substituting moiety" includes moieties which can be placed at any one of the $R_4$, $R_6$, $R_8$ or $R_9$ positions without prohibitively detrimentally affecting the synthesis of the antibiotic. In an advantageous embodiment, each substituting moiety is selected such that the oxazinone formed may perform its intended function. Examples of substituting moieties include alkyl, hydrogen and other substituents which are not detrimental to the synthesis of olefinic oxazinone. Examples of substituting moieties include alkyl (e.g., lower alkyl) and hydrogen. In one embodiment, $R_8$ and $R_9$ are both hydrogen.

In one embodiment, the olefinic oxazinone of formula (I) has the R configuration at the * carbon. In another further embodiment, the olefinic oxazinone of formula (I) has the S configuration at the * carbon as shown in the formulae below:

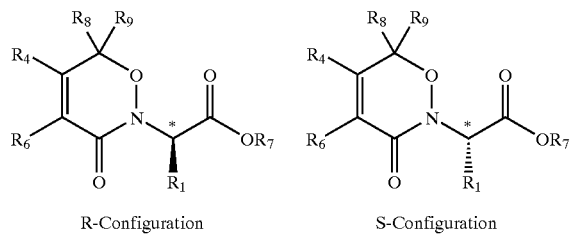

R-Configuration    S-Configuration

In one embodiment, $R_7$ is hydrogen. In another embodiment, $R_4$ is hydrogen or lower alkyl (e.g., methyl, ethyl, propyl, etc.). In another embodiment, $R_6$ is hydrogen or lower alkyl (e.g., methyl, ethyl, propyl, etc.).

The invention also pertains, at least in part to a method for synthesizing oxazinones of the formula (II):

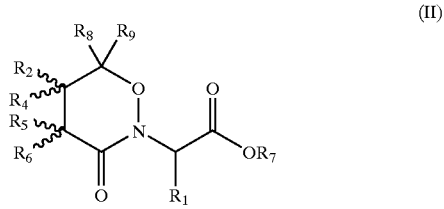

(II)

wherein:
$R_1$ is an amino acid side chain mimicking moiety;
$R_2$ is halogen, OH, SH, $NH_2$, $NHCOR_3$, or an electronegative moiety;
$R_3$ is an antibacterial substituent;
$R_4$, $R_8$ and $R_9$ are each independently selected substituting moieties;
$R_5$ is OH, $NH_2$, $NHCOR_3$, or an electronegative moiety; and
$R_6$ is a substituting moiety or the oxygen of a carbonyl group when taken together with $R_5$;

$R_7$ is hydrogen, a protecting moiety, or a prodrug moiety, and pharmaceutically acceptable salts and esters thereof.

In a further embodiment, compounds of formula (II) include compounds wherein $R_8$ and $R_9$ are each hydrogen, $R_4$ is hydrogen or alkyl (e.g., lower alkyl) and $R_6$ is hydrogen, lower alkyl, or the oxygen of a carbonyl group when taken together with $R_5$.

The method includes contacting an olefinic oxazinone of formula (I) with a derivatizing agent, under appropriate conditions such that an oxazinone of formula (II) is synthesized.

The term "derivatizing agent" includes reagents and catalysts which can be used to derivatize the olefinic bond of the olefinic oxazinone compound. Methods for the derivatization of olefinic bonds are known in the art (for examples, see, Smith & March, *March's Advanced Organic Chemistry*, John Wiley & Sons, New York, 2001, and references cited therein). The term also includes combinations and sequences of derivatizing agents which form the desired oxazinone through multistep syntheses from the olefinic oxazinone. For example, in one embodiment, the olefinic oxazinone is contacted with a derivatizing agent under conditions such that an oxazinone epoxide is formed. Then, the epoxide is reacted with another derivatizing agent, under conditions such that the desired oxazinone is formed.

Examples of derivatizing agents include those which selectively aminohydroxylate the olefinic bond of the olefinic oxazinone, e.g., $(DHQD)_2PHAL$, $(DHQD)_2AQN$, $(DHQ)_2PHAL$, $(DHQ)_2AQN$ (see, for example, Tao et al. *Tet. Lett.* (1998) 39:2507; O'Brien, et al. *Angew. Chem. Int. Ed.* (1999) 38(3):326; Brunko et al. *Angew. Chem. Int. Ed. Engl.* (1997) 36(13/14):1483). Also included are agents which dihydroxylate the olefinic bond to form the diol. Examples include dihydroquinine p-chlorobenzoate and $OsO_4$ (Wang et al. *J. Am. Chem. Soc.* (1992) 114:7568). Other methods are also well known in the art (see, for examples, see, Smith & March, *March's Advanced Organic Chemistry*, John Wiley & Sons, New York, 2001, and references cited therein). Other derivatizing agents include those which selectively halogenate the olefinic bond (e.g., N-fluoropyridium salt (Umemoto et al. *J. Am. Chem. Soc.* (1990) 112:8563, as well as others known in the art).

In one embodiment, an oxazinone epoxide is formed when the derivatizing agent contacts the olefinic oxazinone under appropriate conditions. In a second embodiment, an oxazinone epoxide is formed by a two-step process, comprising contacting the olefinic oxazinone with a hypohalous acid (e.g., HOF, HOBr, HOCl, or HOI), and then subsequently with a base (e.g., potassium carbonate).

Examples of oxazinone epoxides include compounds of formulae (III) and (IV):

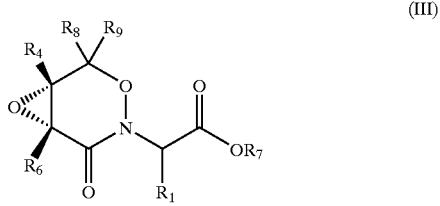

(III)

-continued

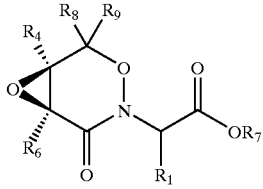
(IV)

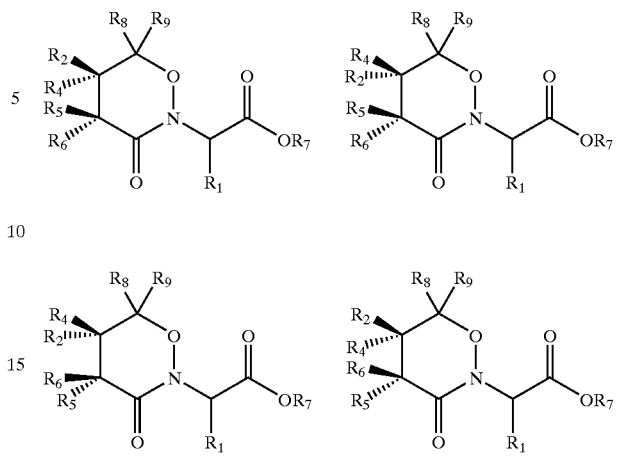

The epoxide oxazinone can be formed using enantioselective epoxidation techniques known in the art. For example, the epoxidation can be performed using the Sharpless asymmetric epoxidation with t-BuOOH, titanium tetraisopropoxide and optically active diethyl tartrate included as the derivatizing agents (see, Sharpless et al. *Pure Appl. Chem.* (1983) 55:1823; Pfenninger *Synthesis* (1986) 89). Alternatively, the epoxide oxazinone can be formed using various oxidizing agents (e.g., sodium hypochlorite) and optically active mangenese or cobalt catalysts such as manganese-salen or salen (II) cobalt complexes as the derivatizing agents (see, Jacobson et al. *J. Am. Chem. Soc.* (1991) 113:7063; Hatayama et al. *Synlett* (1992) 407; Linker *ACIEE* (1997) 36:2060).

The epoxide oxazinones can then be converted further with additional derivatizing agents (e.g., epoxide opening agents) under appropriate conditions to yield the desired oxazinone. Examples of epoxide opening agents include various nucleophiles, water (see, Kotsuki et al. *Tet. Lett.* (1993) 34:4031; Furrow et al. *J. Org. Chem.*, (1998) 63:6776 for stereo- and enantioselective ring opening), ammonia (see, Hou et al. *Tetrahedron Asymmetry*, (1998) 9:1747; and Meguro *J. Chem. Soc. Perkin. Trans.* 1, (1994) 2597 for stereo- and enantioselective ring opening), hydrohalic acids (e.g., HF, HBr, HCl, HI) (see, Olah, *Isr. J. Chem.* (1978) 17:148; Shimizu et al. *Tett. Lett.* (1988) 29:4101), hydrogenating agents (e.g., $SmI_2$ (Molander et al. *J. Org. Chem.*, (1986) 51:5259), Red-Al (Gao et al. *J. Org. Chem.* (1988) 53:4081), $H_2$ and a Pd-phosphine catalyst, etc. (Oshima et al. *J. Am. Chem. Soc.* (1989) 111:6280), etc. These reactions may be performed under conditions such that the resulting oxazinone is stereo- and/or enantiospecifically synthesized. Many methods known in the art for converting epoxides to other chemical functional groups are available (see, for example, Smith & March, *Advanced Organic Chemistry*, John Wiley & Sons, New York, 2001).

The term "appropriate conditions" includes the conditions for the various chemical reactions which result in the desired product (or intermediate to be formed). For example, appropriate conditions includes choice of solvent (e.g., polar, non-polar, etc.), atmosphere (e.g., Ar, $N_2$, etc.), temperature, pressure, etc. One of ordinary skill in the art will be able to use the techniques described in the application and/or the chemical literature to determine what the appropriate conditions for a particular reaction are. Furthermore, the desired oxazinone may require additional steps such as purification (e.g., by techniques known in the art, such as, but not limited to column chromatography, preparative HPLC, distillation, recrystallization, etc.) such that the desired oxazinone is obtained at the desired purity.

The term "antibacterial substituent" includes substituents which are known to enhance the biological activity of penicillins or cephalosporin. Examples of such substituents are given in U.S. Pat. No. 4,013,653, U.S. Pat. No. 4,775,670; and U.S. Pat. No. 4,822,788, incorporated herein by reference in their entirety.

The term "electronegative substituent" includes substituents which are more electron withdrawing than hydrogen. Examples of electronegative substituents include carboxylic acids, halogens (e.g., fluorine, bromine, chlorine, and iodine), aryloxy groups, esters, ethers, ketones, thiols, thiethers, hydroxyl groups, aryl groups, alkenyl groups, etc.

The invention also pertains, at least in part, to methods for the synthesis of an olefinic oxazinone of formula (I). One of the methods includes contacting a diolefin with a cyclization catalyst under appropriate conditions, such that an olefinic oxazinone is formed. The diolefin is of formula (V):

(V)

wherein:

$R_1$ is an amino acid side chain mimicking moiety;

$R_4$, $R_6$, $R_8$ and $R_9$ are each independently selected substituting moieties;

$R_7$ is hydrogen, a protecting moiety, or a prodrug moiety, and acceptable salts and esters thereof. In a further embodiment, $R_8$ and $R_9$ are both hydrogen.

The term "cyclization catalyst" includes catalysts known in the art which are capable of cyclizing a diolefin to form a olefinic ring. In one embodiment, the cyclization catalyst is Grubb's Catalyst, e.g., bis(tricyclohexylphosphine) benzylidene ruthenium dichloride.

The term "appropriate conditions" include those conditions which allow the reaction to take place. For example, for this reaction appropriate conditions include those which result in the olefinic oxazinone being formed. Examples of appropriate solvents include non-polar solvents such as methylene chloride and benzene. However, it should be noted that the appropriate conditions are reaction specific and an ordinarily skilled artisan will be able to use the teachings herein as well as the chemical literature, if necessary, to determine the optimal conditions for his/her particular reaction.

The invention also pertains to a method for the synthesis of an olefinic oxazinone of formula (I) by treating an olefinic triphenyl phosphine salt (e.g., triflic salt) with ozone under appropriate conditions, such that an olefinic oxazinone is formed. The olefinic triphenyl phosphine salt is of formula (VI)

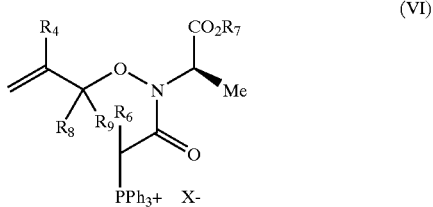

wherein:
$R_1$ is an amino acid side chain mimicking moiety;
$R_4$, $R_6$, $R_8$, and $R_9$ are each independently selected substituting moieties;
$R_7$ is hydrogen, a protecting moiety, or a prodrug moiety, and pharmaceutically acceptable salts and esters thereof. In a further embodiment, $R_8$ and $R_9$ are both hydrogen.

The term "alkyl" includes saturated aliphatic groups, including straight-chain alkyl groups (e.g., methyl, ethyl, propyl, butyl, pentyl, hexyl, heptyl, octyl, nonyl, decyl. etc.), branched-chain alkyl groups (e.g., isopropyl, tert-butyl, isobutyl, etc.), cycloalkyl (alicyclic) groups (e.g., cyclopropyl, cyclopentyl, cyclohexyl, cycloheptyl, cyclooctyl), alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone. In certain embodiments, a straight chain or branched chain alkyl has 6 or fewer carbon atoms in its backbone (e.g., $C_1$–$C_6$ for straight chain, $C_3$–$C_6$ for branched chain), and more preferably 4 or fewer. Likewise, preferred cycloalkyls have from 3–8 carbon atoms in their ring structure, and more preferably have 5 or 6 carbons in the ring structure. The term $C_1$–$C_6$ includes alkyl groups containing 1 to 6 carbon atoms.

Moreover, the term alkyl includes both "unsubstituted alkyls" and "substituted alkyls", the latter of which refers to alkyl moieties having substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "arylalkyl" moiety is an alkyl substituted with an aryl (e.g., phenylmethyl (benzyl)). The term "alkyl" also includes the side chains of natural and unnatural amino acids.

The term "aryl" includes groups, including 5- and 6-membered single-ring aromatic groups that may include from zero to four heteroatoms, for example, benzene, phenyl, pyrrole, furan, thiophene, thiazole, isothiazole, imidazole, triazole, tetrazole, pyrazole, oxazole, isoxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzimidazole, benzthiophene, methylenedioxyphenyl, quinoline, isoquinoline, naphthridine, indole, benzofuran, purine, benzofuran, diazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, arylalkylcarbonyl, alkenylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The term "alkenyl" includes unsaturated aliphatic groups analogous in length and possible substitution to the alkyls described above, but that contain at least one double bond.

For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl further includes alkenyl groups which include oxygen, nitrogen, sulfur or phosphorous atoms replacing one or more carbons of the hydrocarbon backbone. In certain embodiments, a straight chain or branched chain alkenyl group has 6 or fewer carbon atoms in its backbone (e.g., $C_2$–$C_6$ for straight chain, $C_3$–$C_6$ for branched chain). Likewise, cycloalkenyl groups may have from 3–8 carbon atoms in their ring structure, and more preferably have 5 or 6 carbons in the ring structure. The term $C_2$–$C_6$ includes alkenyl groups containing 2 to 6 carbon atoms.

Moreover, the term alkenyl includes both "unsubstituted alkenyls" and "substituted alkenyls", the latter of which refers to alkenyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond.

For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups which include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$–$C_6$ for straight chain, $C_3$–$C_6$ for branched chain). The term $C_2$–$C_6$ includes alkynyl groups containing 2 to 6 carbon atoms.

Moreover, the term alkynyl includes both "unsubstituted alkynyls" and "substituted alkynyls", the latter of which refers to alkynyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including, e.g., alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" as used herein means an alkyl group, as defined above, but having from one to five carbon atoms in its backbone structure. "Lower alkenyl" and "lower alkynyl" have chain lengths of, for example, 2–5 carbon atoms.

The term "acyl" includes compounds and moieties which contain the acyl radical ($CH_3CO$—) or a carbonyl group. The term "substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "acylamino" includes structures wherein an acyl moiety is bonded to an amino group. For example, the term includes alkylcarbonylamino, arylcarbonylamino, carbamoyl and ureido groups.

The term "aroyl" includes compounds and moieties with an aryl or heteroaromatic moiety bound to a carbonyl group. Examples of aroyl groups include phenylcarboxy, naphthyl carboxy, etc.

The terms "alkoxyalkyl", "alkylaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "amine" or "amino" includes compounds where a nitrogen atom is covalently bonded to at least one carbon or heteroatom. The term "alkyl amino" includes groups and compounds wherein the nitrogen is bound to at least one additional alkyl group. The term "dialkyl amino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group which is bound to at least one alkyl group and at least one aryl group. The term "alkylaminoalkyl" refers to an alkyl, alkenyl, or alkynyl group bound to a nitrogen atom which is also bound to an alkyl group.

The term "amide" or "aminocarboxy" includes compounds or moieties which contain a nitrogen atom which is bound to the carbon of a carbonyl or a thiocarbonyl group. The term includes "alkylaminocarboxy" groups which include alkyl, alkenyl, or alkynyl groups bound to an amino group bound to a carboxy group. It includes arylaminocarboxy groups which include aryl or heteroaryl moieties bound to an amino group which is bound to the carbon of a carbonyl or thiocarbonyl group. The terms "alkylaminocarboxy," "alkenylaminocarboxy," "alkynylaminocarboxy," and "arylaminocarboxy" include moieties wherein alkyl, alkenyl, alkynyl and aryl moieties, respectively, are bound to a nitrogen atom which is in turn bound to the carbon of a carbonyl group.

The term "carbonyl" or "carboxy" includes compounds and moieties which contain a carbon connected with a double bond to an oxygen atom. Examples of moieties which contain a carbonyl include aldehydes, ketones, carboxylic acids, amides, esters, anhydrides, etc.

The term "thiocarbonyl" or "thiocarboxy" includes compounds and moieties which contain a carbon connected with a double bond to a sulfur atom.

The term "ether" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or hetero atoms. Examples of thioethers include, but are not limited to alkthioalkyls, alkthioalkenyls, and alkthioalkynyls. The term "alkylthioalkyls" include compounds with an alkyl, alkenyl, or alkynyl group bonded to a sulfur atom which is bonded to an alkyl group. Similarly, the term "alkylthioalkenyls" and alkthioalkynyls" refer to compounds or moieties wherein an alkyl, alkenyl, or alkynyl group is bonded to a sulfur atom which is covalently bonded to an alkynyl group.

The term "hydroxy" or "hydroxyl" includes groups with an —OH or —O⁻.

The term "halogen" includes fluorine, bromine, chlorine, iodine, etc. The term "perhalogenated" generally refers to a moiety wherein all hydrogens are replaced by halogen atoms.

The terms "polycyclyl" or "polycyclic radical" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminocarbonyl, arylalkylamino-carbonyl, alkenylaminocarbonyl, alkylcarbonyl, arylcarbonyl, arylalkyl carbonyl, alkenylcarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" includes atoms of any element other than carbon or hydrogen. Preferred heteroatoms are nitrogen, oxygen, sulfur and phosphorus.

It will be noted that the structure of some of the compounds of this invention includes asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis.

Furthermore, the structures and other compounds and moieties discussed in this application also include all tautomers thereof.

In another embodiment, the invention pertains to a method for treating a bacterial associated state in a subject. The method includes administering to said subject an effective amount of an oxazinone compound of the invention, e.g., a compound of formula (I), (II), (III), (IV) or otherwise described herein.

The term "treating" includes curing as well as ameliorating at least one symptom of the state, disease or disorder.

The term "subject" includes organisms capable of suffering from an bacterial associated state, such as mammals (e.g. primates (e.g., monkeys, gorillas, chimpanzees, and, advantageously, humans), goats, cattle, horses, sheep, dogs, cats, mice, rabbits, pigs, dolphins, ferrets, squirrels), reptiles, or fish. In a further embodiment, the subject is suffering from the bacterial associated disorder at the time of administering the oxazinone compound of the invention.

The term "administering" includes routes of administration which allow the oxazinone compound to perform its intended function. Examples of routes of administration which can be used include parental injection (e.g., subcutaneous, intravenous, and intramuscular), intraperitoneal injection, oral, inhalation, and transdermal. The injection can be bolus injections or can be continuous infusion. Depending on the route of administration, the oxazinone compound can be coated with or disposed in a selected material to protect it from natural conditions which may detrimentally effect its ability to perform its intended function. The oxazinone compound can be administered alone, with a pharmaceutically acceptable carrier, or in combination with a supplementary compound, e.g., an antibiotic, e.g., penicillin or cephalosporin. The oxazinone compound can be administered prior to the onset of an bacterial associated state, or after the onset of a bacterial associated state. The oxazinone compound also can be administered as a prodrug which is converted to another (e.g., active) form in vivo.

The term "bacterial associated state" includes states characterized by the presence of Gram-positive pathogens, for example Staphylococci, Enterococci, Streptococci and mycobacteria. In a further embodiment, the bacterial associated state is associated with a bacterial strain which is resistant to conventional antibiotics. Examples of such strains include methicillin resistant staphylococcus (MRSA), methicillin resistant coagulase negative staphylococci (MRCNS), penicillin resistant *streptococcus pneumoniae* and multiply resistant *Enterococcus faecium*.

In a further embodiment, the oxazinone compound of the invention is administered in combination with a pharmaceutically acceptable carrier.

In another further embodiment, the oxazinone compound is administered in combination with a supplementary compound. Examples of supplementary compounds include antibiotics such a penicillin, methicillin, cephalosphorin, vancomycin, etc.

The term "in combination with" a supplementary compound is intended to include simultaneous administration of the oxazinone compound and the supplementary compound, administration of the oxazinone compound first, followed by the supplementary compound, and administration of the supplementary compound first, followed by the oxazinone compound second. Any of the therapeutically useful compound known in the art for treating a particular bacterial associated state can be used in the methods of the invention.

In yet another embodiment, the invention includes pharmaceutical compositions comprising an effective amount of a compound of the invention, e.g., a compound of formula (I), (II), (III), (IV), or otherwise described herein.

In a further embodiment, the pharmaceutical composition of the invention includes a pharmaceutically acceptable carrier and/or a supplementary agent, e.g., an antibiotic. In further embodiment, the effective amount of the oxazinone compound is effective to treat a bacterial infection of a subject, e.g., a human.

The invention also pertains to pharmaceutical compositions comprising a therapeutically effective amount of a compound of the invention and, optionally, a pharmaceutically acceptable carrier.

The language "pharmaceutically acceptable carrier" includes substances capable of being coadministered with the compound(s) of the invention, and which allow both to perform their intended function. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds of the invention.

The compounds of the invention that are basic in nature are capable of forming a wide variety of salts with various inorganic and organic acids. The acids that may be used to prepare pharmaceutically acceptable acid addition salts of the compounds of the invention that are basic in nature are those that form non-toxic acid addition salts, i.e., salts containing pharmaceutically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and palmoate [i.e., 1,1'-methylene-bis-(2-hydroxy-3-naphthoate)] salts. Although such salts must be pharmaceutically acceptable for administration to a subject, e.g., a mammal, it is often desirable in practice to initially isolate a compound of the invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The preparation of other compounds of the invention not specifically described in the foregoing experimental section can be accomplished using combinations of the reactions described above that will be apparent to those skilled in the art.

The compounds of the invention that are acidic in nature are capable of forming a wide variety of base salts. The chemical bases that may be used as reagents to prepare pharmaceutically acceptable base salts of those compounds of the invention that are acidic in nature are those that form non-toxic base salts with such compounds. Such non-toxic base salts include, but are not limited to those derived from such pharmaceutically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines. The pharmaceutically acceptable base addition salts of compounds of the invention that are acidic in nature may be formed with pharmaceutically acceptable cations by conventional methods. Thus, these salts may be readily prepared by treating the compound of the invention with an aqueous solution of the desired pharmaceutically acceptable cation and evaporating the resulting solution to dryness, preferably under reduced pressure. Alternatively, a lower alkyl alcohol solution of the compound of the invention may be mixed with an alkoxide of the desired metal and the solution subsequently evaporated to dryness.

The compounds of the invention and pharmaceutically acceptable salts thereof can be administered via either the oral, parenteral or topical routes. In general, these compounds are most desirably administered in effective dosages, depending upon the weight and condition of the subject being treated and the particular route of administration chosen. Variations may occur depending upon the species of the subject being treated and its individual response to said medicament, as well as on the type of pharmaceutical formulation chosen and the time period and interval at which such administration is carried out.

The compounds of the invention may be administered alone or in combination with pharmaceutically acceptable carriers or diluents by any of the routes previously mentioned, and the administration may be carried out in single or multiple doses. For example, the novel therapeutic agents of this invention can be administered advantageously in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration (including intraperitoneal, subcutaneous, intravenous, intradermal or intramuscular injection), solutions of a therapeutic compound of the present invention in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art. For parenteral application, examples of suitable preparations include solutions, preferably oily or aqueous solutions as well as suspensions, emulsions, or implants, including suppositories. Therapeutic compounds may be formulated in sterile form in multiple or single dose formats such as being dispersed in a fluid carrier such as sterile physiological saline or 5% saline dextrose solutions commonly used with injectables.

Additionally, it is also possible to administer the compounds of the present invention topically when treating inflammatory conditions of the skin. Examples of methods of topical administration include transdermal, buccal or sublingual application. For topical applications, therapeutic compounds can be suitably admixed in a pharmacologically inert topical carrier such as a gel, an ointment, a lotion or a cream. Such topical carriers include water, glycerol, alcohol, propylene glycol, fatty alcohols, triglycerides, fatty acid esters, or mineral oils. Other possible topical carriers are liquid petrolatum, isopropylpalmitate, polyethylene glycol, ethanol 95%, polyoxyethylene monolauriate 5% in water, sodium lauryl sulfate 5% in water, and the like. In addition, materials such as anti-oxidants, humectants, viscosity stabilizers and the like also may be added if desired.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

In addition to treatment of human subjects, the therapeutic methods of the invention also will have significant veterinary applications, e.g. for treatment of livestock such as cattle, sheep, goats, cows, swine and the like; poultry such as chickens, ducks, geese, turkeys and the like; horses; and pets such as dogs and cats. Also, the compounds of the invention may be used to treat non-animal subjects, such as plants.

It will be appreciated that the actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines.

EXEMPLIFICATION OF THE INVENTION

Example 1
Synthesis of Olefinic Oxazinones of the Invention

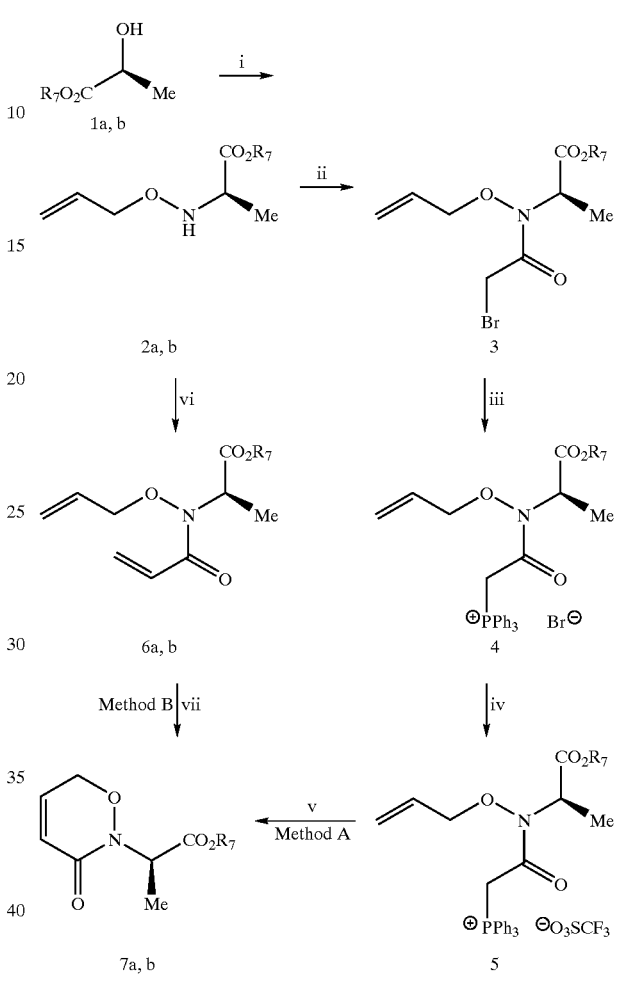

a $R_7$ = PhCH$_2$
b $R_7$ = Bu$^t$

Reagents: (i) (CF$_3$SO$_2$)$_2$O, 2,6-lutidine, O-allylhydroxylamine, CH$_2$Cl$_2$; (ii) BrCH$_2$COBr, Et$_3$N, CH$_2$Cl$_2$; (iii) PPh$_3$, toluene; (iv) CF$_3$SO$_3$Ag, MeCN; (v) 1) O$_3$, CH$_2$Cl$_2$, 2) Me$_2$S, 3) K$_2$CO$_3$, H$_2$O; (vi) CH$_2$=CHCOCl, Et$_3$N or 2,6-lutidine, CH$_2$Cl$_2$; (vii) PhCH=RuCl$_2$[P(Cychex)$_3$]$_2$(Grubbs' catalyst), CH$_2$Cl$_2$ of benzene.

(R)-N-Allyloxyalanine benzyl ester (2a). A solution of triflic anhydride (10.86 g, 38.5 mmol) in dry CH$_2$Cl$_2$ (20 mL) was added dropwise to a solution of benzyl (S)-lactate (1a) (6.31 g, 35 mmol) in dry CH$_2$Cl$_2$ (100 mL) with cooling (−68~−72° C.) and stirring. After 5~7 min, a solution of 2,6-lutidine (4.31 g, 40.3 mmol) in dry CH$_2$Cl$_2$ (15 mL) was added dropwise at the same temperature and the reaction mixture was stirred for 30 min at −68~−72° C. A solution of O-allylhydroxylamine (4.55 g, 77 mmol) in dry CH$_2$Cl$_2$ (15 mL) was added dropwise to the prepared solution of the alkylating reagent with cooling (−68~−72° C.) and stirring. The reaction mixture was stirred for 15 min at ca. −72° C. and then was allowed to warm up to RT. After stirring for 15 h at RT, the reaction mixture was thoroughly shaken with sat. aqueous NaHCO$_3$ (200 mL) and dried over MgSO$_4$. After removal of the solvent, the residue was purified by dry flash chromatography (Silica Gel 60H for TLC, 10%

EtOAc-hexanes) to afford 8.20 g (99.6%) of the product 2a as a pale yellowish oil. $^1$H NMR (100 MHz) in CDCl$_3$+1 drop of D$_2$O (J, Hz): δ 1.28 (3H, d, $^3$J=7.1, MeCH), 3.82 (1H, q, $^3$J=7.1, MeCH), 4.22 (2H, dt, $^3$J=5.7, $^4$J=1.2, OCH$_2$CH=CH$_2$), 5.16–5.37 (2H, m, CH=CH$_2$), 5.23 (2H, CH$_2$Ph), 5.76–6.15 (1H, m, $^3$J=5.7, $^3$J$^{cis}$=9.9, $^3$J$^{trans}$=17.1, CH=CH$_2$), 7.38 (5H, Ph). $^{13}$C (100 MHz) in CDCl$_3$: δ 14.81, 59.09, 66.63, 75.22, 117.53, 128.06, 128.24, 128.56, 134.37, 135.84, 174.01. IR (film), cm$^{-1}$: 3264, 1740, 1456, 1208, 1170. Anal. Calcd for C$_{13}$H$_{17}$NO$_3$: C, 66.4; H, 7.3; N, 5.95. Found: C, 66.3; H, 7.4; N, 6.15%.

(R)-N-(Bromoacetyl)-N-allyloxyalanine benzyl ester (3). To a solution of (R)-N-allyloxyalanine benzyl ester (2a) (2.59 g, 11 mmol) and Et$_3$N (1.11 g, 11 mmol) in dry CH$_2$Cl$_2$ (30 mL), a solution of bromoacetyl bromide (2.22 g, 11 mmol) in dry CH$_2$Cl$_2$ (20 mL) was added dropwise with cooling (−25~−30° C.) and stirring. The reaction mixture was stirred for 1 h at 0~+5° C. and allowed to warm up to RT. After dilution with CH$_2$Cl$_2$ (ca. 30 mL), the mixture was washed with water (2×30 mL), 1N HCl (30 mL), sat. aq. NaHCO$_3$ (30 mL), and dried over MgSO$_4$. Removal of the solvent afforded 3.90 g (99%) of the product 3 as a yellowish oil. $^1$H NMR (100 MHz) in CDCl$_3$ (J, Hz): δ 1.60 (3H, d, $^3$J=7.3, MeCH), 4.08 (2H, dd, $^3$J=6.1, $^4$J=0.9, OCH$_2$CH=CH$_2$), 4.49 (2H, dt, $^3$J=6.1, $^4$J=0.9, OCH$_2$CH=CH$_2$), 4.98 (1H, q, MeCH, $^3$J=7.3), 5.16–5.48 (2H, m, CH=CH$_2$), 5.20 (2H, CH$_2$Ph), 5.76–6.15 (1H, m, $^3$J=6.1, $^3$J$^{cis}$=10.0, $^3$J$^{trans}$=17.3, CH=CH$_2$), 7.29–7.41 (5H, m, Ph). IR (film), cm$^{-1}$: 1746, 1678, 1455, 1214. MS (CI, isobutane), m/Z: 357 (M$^+$+1), 356 (M$^+$).

(R)-N-(2-triphenylphosphonio)acetyl-N-allyloxyalanine benzyl ester bromide or (R)-{[N-Allyloxy-N-(α-benzoxycarbonylethyl) carbamoyl]methyl}triphenylphosphonium bromide (4). A solution of (R)—N-(Bromoacetyl)-N-allyloxyalanine benzyl ester (3) (3.90 g, 11 mmol) in dry toluene (10 mL) was added portionwise to a solution of triphenylphosphine (2.885 g, 11 mmol) in dry toluene (20 mL) and the reaction mixture was stirred for 24 hours at room temperature. The precipitated yellow oil was separated and washed with toluene and dried in vacuo to give a solid yellowish hygroscopic foam, which was reprecipitated from a mixture of dry CH$_2$Cl$_2$ (10 mL) and absolute ether (ca. 100 mL) to afford 5.16 g (76%) the product 4 as a white hygroscopic foam.

(R)-N-(2-triphenylphosphonio)acetyl-N-allyloxyalanine benzyl ester trifluoro methanesulfonate or (R)-{[N-Allyloxy-N-(α-benzoxycarbonylethyl) carbamoyl] methyl}triphenylphosphonium trifluoromethanesulfonate (5). To a solution of (R)-N-(2-triphenylphosphonio)acetyl-N-allyloxyalanine benzyl ester bromide (4) (6.18 g, 10 mmol) in dry MeCN (25 mL), a solution of silver trifluoromethanesulfonate (2.56 g, 10 mmol) in dry MeCN (20 mL) was added portionwise with stirring and the yellow precipitate (AgBr) was filtered off using a glass-sintered funnel with a short pad of Celite 545 and was washed with MeCN (ca. 50 mL). The filtrate was evaporated in vacuo and the residue (yellow foam) was dissolved in CH$_2$Cl$_2$ (100 mL) and some amount of MgSO$_4$ was added to the solution for coagulation of small particles of AgBr. The solution was filtered through a similar funnel as before and the filtrate was evaporated in vacuo to provide 6.52 g (99.5%) of the product 5 as a yellow highly hygroscopic foam. $^1$H NMR (400 MHz) in CDCl$_3$ (J, Hz), major isomer: δ 1.50 (3H, d, $^3$J=7.4, MeCH), 4.84 (1H, dd, $^2$J=11.5, $^3$J=6.1, OCH$_A$CH=CH$_2$), 4.80 (1H, q, MeCH, $^3$J=7.4), 4.84 (1H, dd, $^2$J=11.5, $^3$J=6.1, OCH$_B$CH=CH$_2$), 4.89 (1H, dd, $^2$J$_{HH}$=17.8, $^2$J$_{HP}$=12.7, CH$_A$P), 5.06 (1H, d, $^2$J=12.4, CH$_A$Ph), 5.10 (1H, d, $^2$J=12.4, CH$_B$Ph), 5.31 (1H, br.d, $^3$J$^{cis}$=10.4, CH=CH$_D$), 5.35 (1H, dd, $^2$J$_{HH}$=17.8, $^2$J$_{HP}$=13.8, CH$_B$P), 5.49 (1H, dd, $^3$J$^{trans}$=17.2, $^2$J=1.2, CH=CH$_E$), 5.92–6.02 (1H, m, $^3$J=6.1, $^3$J$^{cis}$=10.4, $^3$J$^{trans}$=17.2, CH=CH$_2$), 7.4–7.8 (5H, m, PhCH$_2$), 7.6–7.7 (15H, m, Ph$_3$P).

(R)-N-Acryloyl-N-allyloxyalanine benzyl ester (6a). To a solution of (R)-N-allyloxyalanine benzyl ester (2a) (7.06 g, 30 mmol) and Et$_3$N (4.55 g, 45 mmol) in dry CH$_2$Cl$_2$ (80 mL), a solution of acryloyl chloride (3.26 g, 36 mmol) in dry CH$_2$Cl$_2$ (20 mL) was added dropwise with cooling (−5~−10° C.) and stirring. The reaction mixture was stirred for 1 h at 0~+5° C. and for 4.5 hours at room temperature. After dilution with CH$_2$Cl$_2$ (ca. 150 mL), the mixture was washed with water (3×50 mL), 1N HCl (50 mL), brine (100 mL), and dried over MgSO$_4$. Removal of the solvent gave 9.16 g of a yellow oil, which was purified by dry flash chromatography (Silica Gel 60H for TLC, 3% EtOAc-hexanes→15% EtOAc-hexanes) to afford 8.52 g (98%) the product 6a as a colorless oil. $^1$H NMR (100 MHz) in CDCl$_3$ (J, Hz): δ 1.61 (3H, d, $^3$J=7.3, MeCH), 4.45 (2H, dq, $^3$J=6.0, $^4$J=1.1, OCH$_2$CH=CH$_2$), 5.09 (1H, q, $^3$J=7.3, MeCH,), 5.21 (2H, CH$_2$Ph), 5.25–5.47 (2H, m, CH=CH$_2$, allyl), 5.76–6.15 (1H, m, $^3$J=6.0, $^3$J$^{cis}$=10.0, $^3$J$^{trans}$=17.3, CH=CH$_2$, allyl), 5.83 (1H, dd, $^2$J=2.7, $^3$J$^{cis}$=7.6, CH=CH$_A$H$_B$, acryloyl), 6.48 (1H, dd, $^2$J=2.7, $^3$J$^{trans}$=17.2, CH=CH$_A$H$_B$, acryloyl), 6.80 (1H, dd, $^3$J$^{cis}$=7.6, $^3$J$^{trans}$=17.2, CH=CH$_2$, acryloyl) 7.39 (5H, Ph). $^{13}$C (100 MHz) in CDCl$_3$: δ 14.06, 56.45, 67.10, 78.27, 120.28, 126.21, 128.07, 128.21, 128.48, 130.04, 130.91, 135.47, 168.22, 170.35. IR (film), cm$^{-1}$: 1746, 1667, 1621, 1411. MS (CI, isobutane), m/Z: 290 (M$^+$+1). Anal. Calcd for C$_{16}$H$_{19}$NO$_4$: C, 66.4; H, 6.6; N, 4.8. Found: C, 66.4; H, 6.7; N, 5.1%.

(R)-N-Acryloyl-N-allyloxyalanine tert-butyl ester (6b). A solution of triflic anhydride (15.52 g, 55 mmol) in dry CH$_2$Cl$_2$ (25 mL) was added dropwise to a solution of tert-butyl (S)-lactate (1b) (6.71 g, 50 mmol) in dry CH$_2$Cl$_2$ (130 mL) with cooling (−68~−72° C.) and stirring. After 5~7 min, a solution of 2,6-lutidine (6.16 g, 57.5 mmol) in dry CH$_2$Cl$_2$ (20 mL) was added dropwise at the same temperature and the reaction mixture was stirred for 1.5 h at −68~−72° C. A solution of O-allylhydroxylamine (6.57 g, 90 mmol) in dry CH$_2$Cl$_2$ (20 mL) was added dropwise to the prepared solution of the alkylating reagent with cooling (−68~−72° C.) and stirring. The reaction mixture was stirred for 15 minutes at about −72° C. and then was allowed to warm up to room temperature. After stirring for 15 hours at room temperature, the reaction mixture was thoroughly shaken with saturated aqueous NaHCO$_3$ (400 mL) and dried over MgSO$_4$. Removal of the solvent provided 14.31 g of a mixture of (R)-N-allyloxyalanine tert-butyl ester (2b) and 2,6-lutidine (1:0.97 mol/mol), which was used in the next step without further purification.

To a solution of the mixture of (R)-N-allyloxyalanine tert-butyl ester (2b) and 2,6-lutidine in dry CH$_2$Cl$_2$ (100 mL) an additional amount of 2,6-lutidine (2.66 g, 24.8 mmol) was added and the solution was cooled to −15~−20° C. A solution of acryloyl chloride (5.09 g, 56.3 mmol) in dry CH$_2$Cl$_2$ (20 mL) was added dropwise at the same temperature. The reaction mixture was stirred for 1 h at 0~+5° C. and for 20 hours at room temperature. After dilution with CH$_2$Cl$_2$ (about 150 mL), the mixture was washed with water (4×50 mL), 1M citric acid (2×50 mL), saturated aqueous NaHCO$_3$ (2×50 mL) and dried over MgSO$_4$. Removal of the solvent gave 12.73 g of a red oil, which was purified by dry flash chromatography (Silica Gel 60H for TLC, 1% EtOAc—hexanes→7% EtOAc-hexanes) to afford 8.91 g (70%) of the product 6b as a colorless oil. $^1$H NMR (100 MHz) in CDCl$_3$ (J, Hz): δ 1.47 (9H, Me$_3$C), 1.53 (3H, d, $^3J=7.3$, MeCH), 4.48 (2H, dq, $^3J=5.9$, $^4J=1.2$, OCH$_2$CH=CH$_2$), 4.93 (1H, q, $^3J=7.3$, MeCH,), 5.26–5.50 (2H, m, CH=CH$_2$, allyl), 5.76–6.18 (1H, m, $^3J=5.9$, $^3J^{cis}=$ 10.1, $^3J^{trans}=15.6$, CH=CH$_2$, allyl), 5.81 (1H, dd, $^2J=2.6$, $^3J^{cis}=9.5$, CH=CH$_A$H$_B$, acryloyl), 6.46 (1H, dd, $^2J=2.6$, $^3J^{trans}=17.0$, CH=CH$_A$H$_B$, acryloyl), 6.80 (1H, dd, $^3J^{cis}=$ 9.5, $^3J^{trans}=17.0$, CH=CH$_2$, acryloyl). $^{13}$C (100 MHz) in CDCl$_3$: δ 14.12, 27.91, 57.28, 78.22, 81.83, 120.02, 126.42, 129.75, 131.09, 132.41, 168.34, 169.55. IR (film), cm$^{-1}$: 2981, 1738, 1667, 1622, 1411. MS (CI, isobutane), m/Z: 256 (M$^+$+1).

(R)-2-(α-Benzoxycarbonylethyl)-4,5-dehydro-1,2-oxazinan-3-one or (R)-2-(3-Oxo-3,6-dihydro-[1,2]oxazin-2-yl)-propionic acid benzyl ester (7a).

Method A. A solution of (R)-N-(2-triphenylphosphonio) acetyl-N-allyloxyalanine benzyl ester trifluoromethanesulfonate (5) (6.52 g, 9.95 mmol) in CH$_2$Cl$_2$ (180 mL) was cooled to −76~−78° C. and saturated with ozone (a moderate bubbling until a persistent blue color) at the same temperature with stirring. An excess of ozone was removed by bubbling N$_2$ through the reaction mixture at −76~−78° C. and Me$_2$S (3.1 g, 50 mmol) was added portionwise with stirring at the same temperature. The reaction mixture was allowed to warm up to room temperature and a solution of K$_2$CO$_3$ (6.91 g, 50 mmol) in water (20 mL) was added. After a vigorous stirring, the reaction mixture was diluted with water (100 mL) and the organic layer was separated off and washed with water (2×30 mL) and dried over MgSO$_4$. Removal of the solvent gave a yellow semi-solid substance, which was purified by flash chromatography (Silica Gel 60, 20% EtOAc-hexanes) to afford 0.70 g (27%) the product 7a as a colorless oil. $^1$H NMR (400 MHz) in CDCl$_3$ (J, Hz): δ 1.53 (3H, d, $^3J=7.3$, MeCH), 4.46 (1H, dq, $^2J=−15.9$, $^3J=3.4$, $^4J=1.8$, OCH$_A$CH=CH), 4.56 (1H, dq, $^2J=15.9$, $^3J=3.4$, $^4J=1.8$, OCH$_B$CH=CH), 5.15 (1H, d, $^2J=12.4$, CH$_A$Ph), 5.19 (1H, q, MeCH, $^3J=7.3$), 5.22 (1H, d, $^2J=12.4$, CH$_B$Ph), 6.04 (1H, dt, $^3J^{cis}=10.0$, $^4J=1.8$, CH=CHCO), 6.72 (1H, dt, $^3J^{cis}=10.0$, $^3J=3.4$, CH$_2$CH=CHCO), 7.27–7.40 (5H, m, Ph). $^{13}$C (100 MHz) in CDCl$_3$: δ 13.71, 53.57, 67.08, 67.57, 122.32, 128.02, 128.26, 128.52, 135.49, 139.67, 164.64, 170.09. IR (film), cm$^{-1}$: 1745, 1675, 1214, 1189. MS (CI, isobutane), m/Z: 262 (M$^+$+1). Anal. Calcd for C$_{14}$H$_{15}$NO$_4$: C, 64.4; H, 5.8; N, 5.4. Found: C, 64.3; H, 5.85; N, 5.6%.

Method B. A solution of(R)-N-acryloyl-N-allyloxyalanine benzyl ester (6a) (7.32 g, 25.3 mmol) and bis(tricyclohexylphosphine)benzylidene ruthenium dichloride (Grubb's catalyst) (1.04 g, 1.26 mmol, 5 mol %) in dry CH$_2$Cl$_2$ (250 mL) was refluxed with Silica Gel 60H (for TLC) followed by washing with CH$_2$Cl$_2$ (50 mL). After removal of the solvent, the dark oily residue was purified by dry flash chromatography (Silica Gel 60H for TLC, 5% EtOAc-hexanes→15% EtOAc-hexanes) to afford 6.05 g (92%) the olefin 7a identical to that described above.

(R)-2-(α-tert-Butoxycarbonylethyl)-4,5-dehydro-1,2-oxazinan-3-one or (R)-2-(3-Oxo-3,6-dihydro-[1,2]oxazin-2-yl)-propionic acid tert-butyl ester (7b). A solution of (R)-N-acryloyl-N-allyloxyalanine tert-butyl ester (6b) (3.39 g, 13.27 mmol) and bis(tricyclohexylphosphine)benzylidene ruthenium dichloride (Grubb's catalyst) (0.481 g, 0.584 mmol, 4.4 mol %) in dry benzene (120 mL) was refluxed with stirring for 6 hours in N$_2$ atmosphere. Two portions (0.234 g, 0.284 mmol and 0.209 g, 0.254 mmol) of the catalyst were added successively and the reaction mixture was refluxed for 8 hours after each addition. The dark brown reaction mixture was filtered through a short pad of Silica Gel 60H (for TLC) followed by washing with CH$_2$Cl$_2$ (100 mL). After removal of the solvent, the dark oily residue was purified by dry flash chromatography (Silica Gel 60H for TLC, 5% EtOAc-hexanes→20% EtOAc-hexanes) to afford 2.45 g (81%) the olefin 7b as a colored oil. $^1$H NMR (400 MHz) in CDCl$_3$ (J, Hz): δ 1.46 (9H, Me$_3$C), 1.53 (3H, d, $^3J=7.3$, MeCH), 4.49 (1H, dq, $^2J=15.8$, $^3J=3.4$, $^4J=1.8$, OCH$_A$CH=CH), 4.64 (1H, dq, $^2J=−15.8$, $^3J=3.4$, $^4J=1.8$, OCH$_B$CH=CH), 5.03 (1H, q, MeCH, $^3J=7.3$), 6.05 (1H, dt, $^3J^{cis}=10.0$, $^4J=1.8$, CH=CHCO), 6.74 (1H, dt, $^3J^{cis}=10.0$, $^3J=3.4$, CH$_2$CH=CHCO). $^{13}$C (100 MHz) in CDCl$_3$: δ 13.77, 27.95, 54.16, 67.53, 81.82, 122.46, 139.47, 164.67, 169.28. IR (film), cm$^{-1}$: 2979, 1737, 1677, 1368, 1162. MS (CI, isobutane), m/Z: 228 (M$^+$+1). Anal. Calcd for C$_{11}$H$_{17}$NO$_4$: C, 58.1; H, 7.5; N, 6.2. Found: C, 58.4; H, 7.7; N, 6.3%.

Example 2
Alternate Synthesis of Olefinic Oxazinones

SCHEME 3

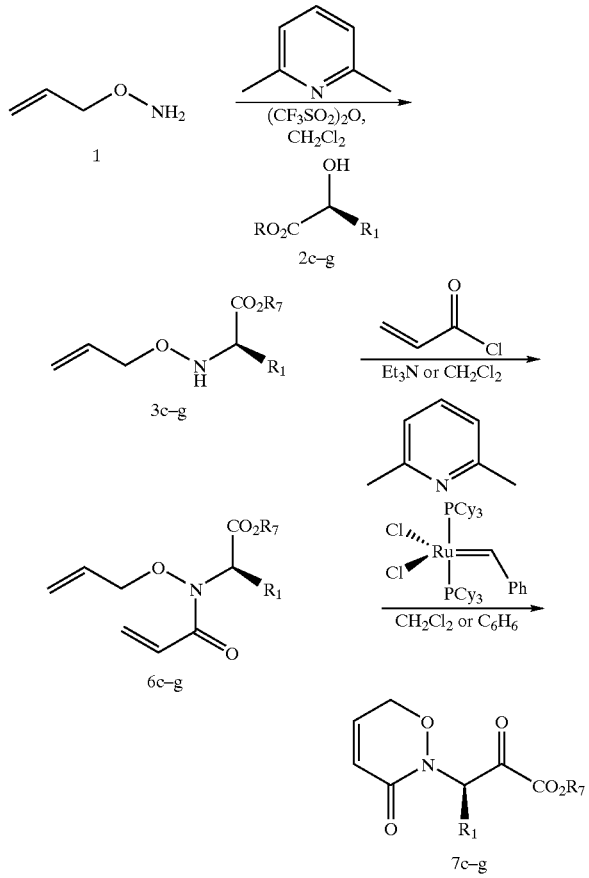

c R$_1$ = CH$_3$ R$_7$ = CH$_2$Ph,
d R$_1$ = CH$_3$ R$_7$ = $^t$Bu
e R$_1$ = CH$_3$ R$_7$ = CHPh$_2$
f R$_1$ = CH(CH$_3$)$_2$ R$_7$ = CHPh$_2$
g R$_1$ = C$_6$H$_5$ R$_7$ = CHPh$_2$,

N-Allyloxyphthalimide. To a cooled solution (5 to 10° C.) of N-hydroxyphthalimide (53.80 g, 0.33 mol) in DMF (120 mL), was added DBU (46.36 mL, 0.31 mol) was added in one portion, with stirring. After 10 minutes, allyl bromide (25.96 mL, 0.30 mol) was added in portions. The cooling bath was removed and the reaction mixture was stirred at room temperature for 1 hour, until the color turned from dark burgundy to yellow. Ethyl acetate (300 mL) and water (150 mL) were added, the aqueous phase was separated, and the organic phase was washed with water (4×50 mL). The combined aqueous extracts were back-extracted with EtOAc (3×50 mL) and the total EtOAc solution was washed with saturated $NaHCO_3$ (10×50 mL) until the aqueous phase was pale yellow, then with brine (2×75 mL) and dried over anhydrous $MgSO_4$. Removal of the solvent afforded 58.83 g (96% yield) of the product as a white solid.

Allyloxyamine. N-Allyloxyphthalimide (58.70 g, 0.289 mol) was dissolved in absolute EtOH (295 mL) with heating and stirring. Then, a solution of $N_2H_4.H_2O$ (14.01 mL, 0.289 mol) in EtOH (44 mL) was added portionwise, with stirring. The reaction mixture immediately turned yellow and a white precipitate formed. The mixture was refluxed for 2 hours, stirred at room temperature for 17 hours, cooled (10 to 15° C.), and concentrated HCl (30.24 mL, 0.369 mol) was added portionwise. The white precipitate was removed by filtration and washed with water (160 mL). The combined filtrates were evaporated under reduced pressure and the residue was maintained at 1 torr for 3 hours. Water (100 mL) was added, the solution was filtered, the filtrate was concentrated to 50 mL and added portionwise to solid KOH pellets in a distillation apparatus. The product was collected at 80–100° C. A second distillation over KOH pellets afforded 18.958 g (89% yield) of the product as a colorless liquid, b.p. 94–97° C.

(S)-2-Hydroxy-3-methylbutyric acid benzhydryl ester (2f). A solution of diphenyldiazomethane (0.70 g, 3.604 mmol) in EtOAc (5 mL) was added portionwise with cooling (ice bath) and stirring to a solution of (S)-2-hydroxy-3-methylbutyric acid (0.51 g, 4.355 mmol) in EtOAc (5 mL). The resulting purple solution was stirred at room temperature for 6 h until color faded to pale yellow, and then was washed successively with saturated aqueous $NaHCO_3$ (3×5 mL) and brine (2×5 ML), dried over anhydrous $MgSO_4$ and evaporated to give 0.9864 g of a yellow solid. Recrystallization from hexanes yielded 0.82 g (80%) of 2f as soft white crystals (m.p. 71–72° C.). $^1$H NMR (400 MHz) in $CDCl_3$ (J, Hz): δ 0.7638 (d, 3H, —$CH_3$), 1.0181 (d, 3H, —$CH_3$), 2.1229–2.2346 (m, 1H, $CHMe_2$), 2.6768 (br. s, 1H, OH), 4.1612 (d, 1H, CHOH), 6.96 (s, 1H, $CHPh_2$), 7.20–7.45 (m, 10H, ArH). MS (CI, isobutane), m/z: 283 ($M^+$). Anal. Calcd. for $C_{18}H_{20}O_3$: C, 76.03; H, 7.09. Found: C, 76.13; H, 7.12%.

(S)-2-Trifluoromethanesulfonyloxy-3-methylbutyric acid benzhydryl ester. A solution of triflic anhydride (4.42 mL, 26.29 mmol) in dry $CH_2Cl_2$ (12 mL) was added dropwise via syringe to a solution of 2f (6.50 g, 22.86 mmol) in dry $CH_2Cl_2$ (70 mL), with cooling (−68 to −70° C.) and stirring. After 5 min, a solution of 2,6-lutidine (3.19 mL, 27.43 mmol) in dry $CH_2Cl_2$ (10 mL) was added dropwise. The pale yellow reaction mixture was stirred at −68° C. for 1 h, warmed to room temperature and stirred for an additional 17 h. The solvent was removed under reduced pressure and the residue (in EtOAc) was washed with 1N citric acid (5×100 mL), dried over anhydrous $MgSO_4$ and evaporated to give 9 g of a red semi-solid. This was purified via dry flash chromatography (Silica Gel 60H for TLC, 5% EtOAc-hexanes) to afford 8.04 g of the triflate as a pale yellow solid. $^1$H NMR (400 MHz) in $CDCl_3$ (J, Hz): δ 0.8878 (d, 3H, —$CH_3$), 1.0479 (d, 3H, —$CH_3$), 2.3842–2.4628 (m, 1H, $CHMe_2$), 5.0431 (d, 1H, $CHOSO_2CF_3$), 7.000 (s, 1H, $CHPh_2$), 7.20–7.42 (m, 10H, ArH). MS (CI, isobutane), m/z: 415 ($M^+$−1). Anal. Calcd. for $C_{19}H_{19}O_5SF_3$: C, 54.80; H, 4.60. Found: C, 54.55; H, 4.63%.

(R)-2-Allyloxyamino-3-methylbutryic acid benzhydryl ester (3f). A solution of O-allyloxylamine (5.414 g, 0.0741 mol) in dry $CH_3CN$ (35 mL) was added, with stirring, to a solution of the triflate (7.711 g, 0.0185 mol) in dry $CH_3CN$ (80 mL). The reaction mixture was refluxed for 3 h, cooled to room temperature, and evaporated under reduced pressure. The residue, in EtOAc (100 mL), was washed successively with saturated $NaHCO_3$ (3×100 mL) and brine (2×100 mL), dried over anhydrous $MgSO_4$ and evaporated to give 6.6720 g of a pale yellow oil. Purification by dry flash chromatography (Silica Gel 60H for TLC, 10% EtOAc-hexanes) afforded 5.6229 g (89%) of 3f as a colorless oil. $^1$H NMR (400 MHz) in $CDCl_3$ (J, Hz): δ 0.8650 (d, 3H, —$CH_3$), 0.9150 (d, 3H, —$CH_3$), 1.8524–1.9379 (m, 1H, $CHMe_2$), 3.5712 (d, 1H, NCH), 4.1667–4.1929 (m, 2H, $OCH_2$), 5.1422–5.1780 (dm, 1H, $OCH_2CH$=CHH), 5.2223 (dd, 1H, $OCH_2CH$=CHH), 5.8281–5.9268 (m, 1H, $OCH_2CH$), 6.975 (s, 1H, $CHPh_2$), 7.23–7.40 (m, 10H, ArH). MS (CI, isobutane), m/z: 340 ($M^+$+1). Anal. Calcd. for $C_{21}H_{25}NO_3$: C, 74.31; H, 7.42; N, 4.13. Found: C, 74.49; H, 7.46; N, 4.40%.

(R)-2-(N-Acryloyl, N-allyloxyamino)-3-methylbutyric acid benzhydryl ester (6f). A solution of 3f (5.085 g, 14.981 mmol) in dry $CH_2Cl_2$ (50 mL) was treated in one portion with triethylamine (3.13 mL, 22.471 mmol. The solution was stirred at room temperature for 5 min, cooled to 0° C. and 97% acryloyl chloride (1.50 mL, 17.977 mmol) was added dropwise via syringe. This mixture was stirred at 0° C. for 45 min, then allowed to warm to room temperature, and stirring was continued for 2.5 h. The light orange reaction mixture was then diluted with $CH_2Cl_2$ (150 mL) and washed successively with water (3×50 mL), N HCl (50 mL) and brine (100 mL), dried over anhydrous $MgSO_4$ and evaporated to 5.6721 g of an orange oil. Purification by dry flash chromatography (Silica Gel 60H for TLC, 3% EtOAc-hexanes→5% EtOAc-hexanes) gave 4.7904 g (81%) of 6f as a yellow oil. $^1$H NMR (400 MHz) in $CDCl_3$ (J, Hz): δ 0.9465 (d, 3H, —$CH_3$), 0.9631 (d, 3H, —$CH_3$), 2.4434–2.5352 (m, 1H, $CHMe_2$), 4.1484 (dd, 1H, OCHH), 4.3206 (dd, 1H, OCHH), 4.8691 (d, 1H, NCH), 5.1729–5.2203 (m, 2H, $OCH_2CH$=$CH_2$), 5.7255–5.8248 (m, 2H, $OCH_2CH$+NC=OCH), 6.4773 (dd, 1H, NC=OCH=CHH), 6.7104 (dd, 1H, NC=OCH=CHH), 6.9054 (s, 1H, $CHPh_2$), 7.20–7.40 (m, 10H, ArH). MS (CI, isobutane), m/z: 397 ($M^+$+1).

(R)-3-Methyl-2-(3-oxo-3,6-dihydro-[1,2]oxazin-2-yl)-butyric acid benzhydryl ester (7f). Bis(tricyclohexylphosphine)benzylidene ruthenium dichloride (0.343 g, 0.417 mmol) was weighed directly into a 250 mL flask, placed under a $N_2$ atmosphere, and dry $CH_2Cl_2$ (25 mL) was added, followed by a solution of 6f (3.279 g, 8.333 mmol) in dry $CH_2Cl_2$ (60 mL). The dark purple reaction mixture was refluxed for 4 h, cooled to room temperature, filtered through a short, densely-packed pad of Silica Gel 60H for thin layer chromatography (φ~3.8 cm, 1~2 cm), which was washed with $CH_2Cl_2$ (5×20 mL). Removal of the solvent gave 3.175 g of a brown oil which was purified via dry flash chromatography (Silica Gel 60H for TLC, 5% EtOAc-hexanes→20% EtOAc-hexanes) to afford 3.5682 g (90%) of 7f as a brown oil. $^1$H NMR (400 MHz) in $CDCl_3$ (J, Hz): δ 0.9897 (d, 3H, —$CH_3$), 1.0067 (d, 3H, —$CH_3$), 2.4435–2.5324 (m, 1H, $CHMe_2$), 4.3791 (ddd, 2H, $NOCH_2$), 4.9721 (d, 1H, NCH), 6.0472 (dt, 1H, $NOCH_2CH$=CH), 6.6793 (dt, 1H, $NOCH_2CH$), 6.9187 (s, 1H, $CHPh_2$), 7.20–7.40 (m, 10H, ArH). MS (CI, isobutane), m/z: 366 ($M^+$+1).

(R)-3-Methyl-2-(3-oxo-3,6-dihydro-[1,2]oxazin-2-yl)-butyric acid (8f, R=H). A solution of 7d (2.00 g, 5.473 mmol) in 98% formic acid (120 mL) was stirred vigorously at room temperature for 6 h. The solvent was then removed in vacuo, and the residue, in dry $CH_2Cl_2$ (100 mL), was dried over anhydrous $MgSO_4$. Removal of the solvent gave 2.2220 g of a yellow oil which was purified via dry flash chromatography (Silica Gel 60H for TLC, 30% EtOAc-hexanes→100% EtOAc) to afford 0.8185 g (75%) of 8f as a yellow solid. $^1$H NMR (100 MHz) in $CDCl_3$ (J, Hz): δ 1.10 (d, 3H, —$CH_3$), 1.15 (d, 3H, —$CH_3$), 2.20–2.80 (m, 1H, $CHMe_2$), 4.40–4.75 (m, 2H, $NOCH_2$), 4.90 (d, 1H, NCH), 6.15 (dt, 1H, $NOCH_2CH$=CH), 6.81 (dt, 1H, $NOCH_2CH$), 8.33 (br. s, 1H, $CO_2H$). MS (CI, isobutane), m/z: 200 ($M^+$).

(R)-3-Methyl-2-(3-oxo-[1,2]oxazinan-2-yl)-butyric acid (9f) A suspension of 10% Pd on activated carbon (0.032 g) in EtOAc (5 mL) was stirred for 1 h in a $H_2$ atmosphere and a solution of 8f (0.032 g, 0.1606 mmol) was added in one portion. This reaction mixture was stirred for 24 hours at room temperature, and then filtered through a densely-packed pad of Silica Gel 60H for thin layer chromatography, which was washed with EtOAc (4×5 mL). Removal of the solvent afforded 0.0193 g (60%) of 9f as a white solid. $^1$H NMR (100 MHz) in $CDCl_3$ (J, Hz): δ 1.02 (d, 3H, —$CH_3$), 1.11 (d, 3H, —$CH_3$), 1.98–2.35 (m, 2H, $NOCH_2CH_2$), 2.35–2.80 (m, 3H, $NOCH_2CH_2CH_2$+$CHMe_2$), 4.00–4.45 (m, 2H, $NOCH_2$), 4.85 (d, 1H, NCH), 6.20 (br. s, 1H, $CO_2H$). MS (CI, isobutane), m/z: 202 ($M^+$).

(S)-Hydroxy-phenylacetic acid benzhydryl ester (2g). A solution of diphenyldiazomethane (0.528 g, 2.719 mmol) in EtOAc (5 mL) was added portionwise with cooling (ice bath) and stirring to a solution of (S)-mandelic acid (0.500 g, 3.286 mmol) in EtOAc (5 mL). The purple reaction mixture was stirred at room temperature for 1 h and was then washed successively with saturated $NaHCO_3$ (3×5 mL) and brine (2×5 mL), dried over anhydrous $MgSO_4$ and evaporated to 0.9864 g of a yellow solid, which was recrystallized from hexanes to give 0.67 g (80%) of 2g. $^1$H NMR (400 MHz) in $CDCl_3$ (J, Hz): δ 3.4515 (d, 1H, OH), 5.2782 (d, 1H, CHOH), 6.75 (s, 1H, $CHPh_2$), 7.20–7.45 (m, 15H, ArH).

(R)-Allyloxyamino phenylacetic acid benzhydryl ester (3g). A solution of triflic anyhydride (10.80 mL, 64.471 mmol) in dry $CH_2Cl_2$ (25 mL) was added dropwise via syringe to a solution of 2g (17.85 g, 56.062 mmol) in dry $CH_2Cl_2$ (175 mL), with cooling (−68 to −70° C.) and stirring. After 5 min, a solution of 2,6-lutidine (7.80 mL, 67.275 mmol) in dry $CH_2Cl_2$ (25 mL) was added dropwise. The pale yellow reaction mixture was stirred at −68° C. for 1 h, and a solution of allyloxyamine (7.294 g, 99.791 mmol) in dry $CH_2Cl_2$ (25 mL) was then added dropwise with continued cooling and stirring. The yellow reaction mixture was stirred for 30 minutes and the cooling bath was then removed and the mixture allowed to warm to room temperature. Stirring was continued at room temperature for 17 hours and the dark yellow solution was mixed in a separatory funnel with 250 mL of saturated $NaHCO_3$. The two layers were gently mixed by bubbling $N_2$ for 20 min, and then by thorough manual shaking. The organic phase was separated, washed successively with saturated $NaHCO_3$ (2×250 mL) and brine (250 mL), dried over anhydrous $MgSO_4$ and evaporated to 24.048 g of a mixture of 3g and 2,6-lutidine (1:0.37 mol:mol), which was used in the next step without further purification. $^1$H NMR (100 MHz) in $CDCl_3$ (J, Hz): δ 4.28 (dt, 2H, $NOCH_2$), 4.95 (br. d, 1H, NCH), 5.10—5.45 (m, 2H, $NOCH_2CH$=$CH_2$), 5.72–6.15 (m, 1H, $NOCH_2CH$), 6.22 (br. d, 1H, NH), 6.98 (s, 1H, $CHPh_2$), 7.02–7.50 (m, 10H, ArH).

(R)-(N-Acryloyl, N-allyloxyamino)-phenylacetic acid benzhydryl ester (6g). 2,6-Lutidine (4.24 mL, 36.3972 mmol) was added dropwise, with stirring, to a solution of 3g (9.0617 g, 24.2648 mmol) in dry $CH_2Cl_2$ (75 mL dry $CH_2Cl_2$ (25 mL). After 5 minutes at room temperature, the reaction mixture was cooled to 0° C. and a solution of 97% acryloyl chloride (2.44 mL, 29.1178 mmol) in dry $CH_2Cl_2$ (25 mL) was added portionwise with stirring. This mixture was stirred at 0° C. for 45 minutes, then allowed to warm to room temperature and stirred for 17 hours. The reaction mixture was then diluted with $CH_2Cl_2$ (50 mL) and washed successively with water (50 mL), N citric acid (2×100 mL), saturated $NaHCO_3$ (2×75 mL) and brine (100 mL), dried over anhydrous $MgSO_4$ and evaporated to a dark orange oil which was purified via dry flash chromatography (Silica Gel 60H for TLC, 3% EtOAc-hexanes→20% EtOAc-hexanes) to afford 6.50 g (32%) of 7g as a yellow oil. $^1$H NMR (400 MHz) in $CDCl_3$ (J, Hz): δ 3.5989 (dd, 1H, NOCHH), 4.0682 (dd, 1H, NOCHH), 5.0355 (dd, 1H, $NOCH_2CH$=CHH), 5.1036 (dd, 1H, $NOCH_2CH$=CHH), 5.5341–5.6340 (m, 1H, $NOCH_2CH$), 5.8435 (dd, 1H, C=OCH), 6.2839 (s, 1H, NCH), 6.4936 (dd, C=OCHCHH), 6.7685 (dd, 1H, C=OCHCHH), 6.9356 (s, 1H, $CHPh_2$), 7.02–7.46 (m, 15H, ArH). MS (CI, isobutane), m/z: 428 ($M^+$+1).

(R)-(3-Oxo-3,6-dihydro-[1,2]oxazin-2-yl)-phenylacetic acid benzhydryl ester (7g). Bis(tricyclohexylphosphine) benzylidene ruthenium dichloride (0.11 g, 0.1289 mmol) was weighed directly into a 50 mL flask, placed under a $N_2$ atmosphere, and dry $CH_2Cl_2$ (10 mL) was added, followed by a solution of 6g (1.1020 g, 2.5778 mmol) in dry $CH_2Cl_2$ (15 mL). The purple reaction mixture was refluxed for 3 h, an additional 0.11 of catalyst was added, and refluxing was continued for another 2 hours. The mixture was then allowed to cool to room temperature and filtered through a short, densely-packed pad of Silica Gel 60H for thin layer chromatography (φ~3.8 cm, 1~2 cm), which was washed with $CH_2Cl_2$ (5×20 mL). Evaporation gave a brown oil which was purified via column chromatography (5% EtOAc-hexanes→30% EtOAc-hexanes) to afford 0.500 g (50% yield) of 7g as a brown oil. $^1$H NMR (400 MHz) in $CDCl_3$ (J, Hz): δ 4.3375 (ddd, 1H, NOCHH), 4.6139 (ddd, 1H, NOCHH), 6.0447 (dt, 1H, $NOCH_2CH$=CH), 6.3715 (s, 1H, NCH), 6.7020 (dt, 1H, $NOCH_2CH$), 6.9626 (s, 1H, $CHPh_2$), 7.10–7.40 (m, 15H, ArH). MS (CI, isobutane), m/z: 400 ($M^+$+1).

(R)-(3-Oxo-3,6-dihydro-[1,2]oxazin-2-yl)-phenylacetic acid (8g). A solution of 7e (0.150 g, 0.3755 mmol) in 98% formic acid (10 mL) was stirred vigorously at room temperature for 6 hours. The solvent was then removed, and any residual acid was co-evaporated with dry $Et_2O$ (2×5 mL). The residue was dissolved in dry $CH_2Cl_2$ (15 mL), dried over anhydrous $MgSO_4$ and evaporated to a yellow oil, which was purified via column chromatography (40%EtOAc-hexanes→100% EtOAc) to afford 0.070 g (80%) of 8g as a brown solid. $^1$H NMR (100 MHz) in $CDCl_3$ (J, Hz): δ 4.41 (ddd, 1H, NOCHH), 4.78 (ddd, 1H, NOCHH), 6.12 (dt, 1H, $NOCH_2CH$=CH), 6.37 (s, 1H, NCH), 6.78 (dt, 1H, $NOCH_2CH$), 7.15–7.60 (m, 5H, ArH), 8.40–9.10 (br. s, 1H, $CO_2H$).

Example 3
Synthesis of Oxazinones from Olefinic Oxazinones

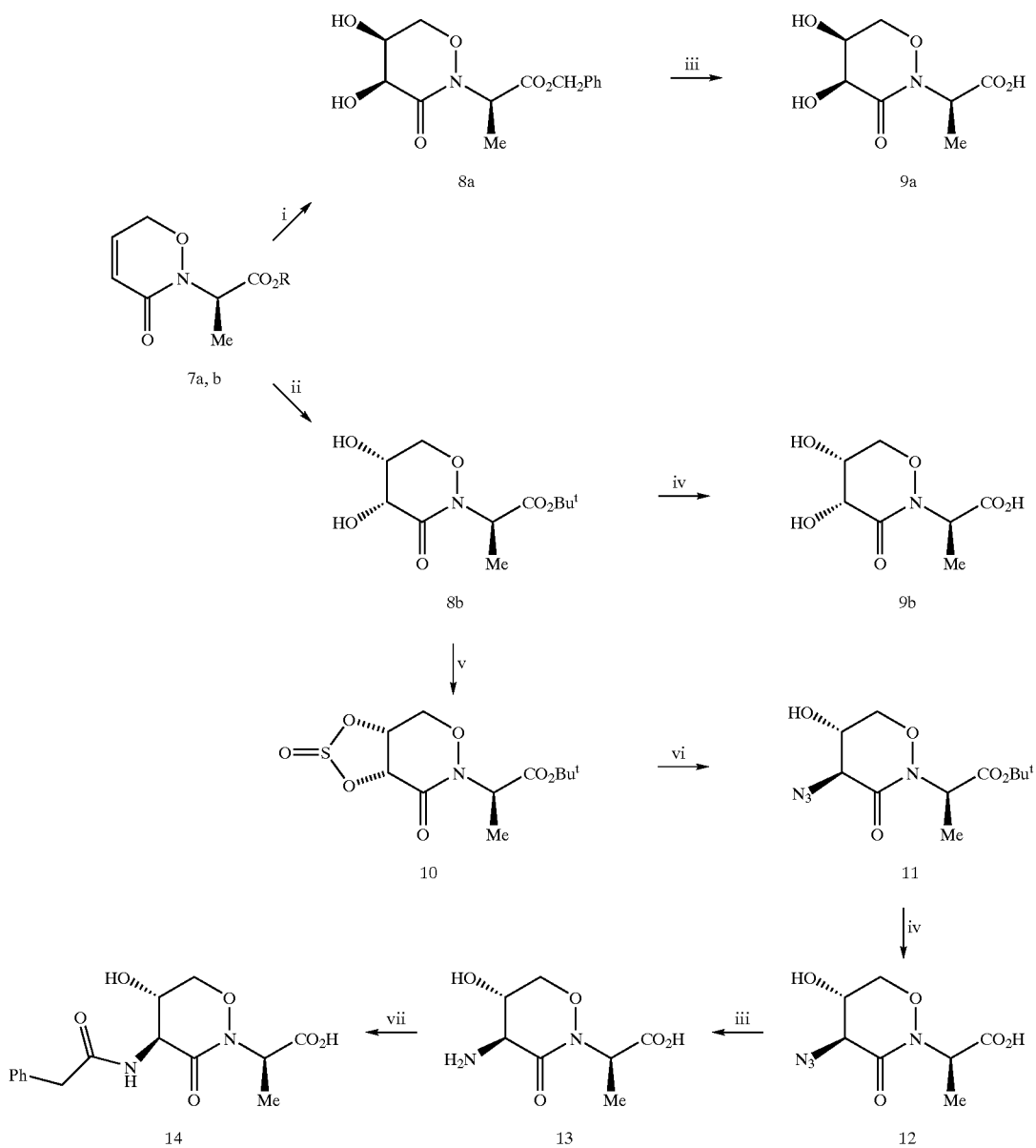

Reagents: (i) AD-mix-β, (DHQD)₂PHAL, K₂OsO₄(OH)₄, MeSO₂NH₂, Bu$^t$OH, H₂O; (ii) AD-mix-α, (DHQ)₂PHAL, K₂OsO₄(OH)₄, MeSO₂NH₂, Bu$^t$OH, H₂O; (iii) H₂, Pd/C, EtOAc; (iv) CF₃CO₂H, CH₂Cl₂; (v) SOCl₂, Et₃N, CH₂Cl₂; (vi) NaN₃, DMF; (vii) PhCH₂COCl, NaHCO₃, MeCN, H₂O.

(αR,4S,5S)-2-(α-Benzoxycarbonylethyl)-4,5-dihydroxy-1,2-oxazinan-3-one (8a). A mixture of K₂OsO₂(OH)₄ (0.0063 g, 0.017 mmol), (DHQD)₂PHAL (0.032 g, 0.041 mmol), and AD-mix-β (1.41 g) was dissolved in a mixture of tert-butanol (5 mL) and water (5 mL). After dissolution of the salts, methanesulfonamide (0.0994 g, 1.04 mmol) was added and the mixture was cooled to −2~0° C. (R)-2-(α-Benzoxycarbonylethyl)-4,5-dehydro-1,2-oxazinan-3-one (7a) (0.264 g, 1.01 mmol) was added in one portion and the heterogeneous slurry was stirred vigorously for 14 h at −2~+2° C. Sodium sulfite (1.5 g) was added in order to quench the oxidation and stirring was continued for 1 h at RT. CH₂Cl₂ (10 mL) was added and the upper organic layer was separated off. The aqueous phase was extracted with CH₂Cl₂ (5×5 mL). The combined organic extracts were dried over MgSO₄. After removal of the solvent, the yellowish semisolid residue was purified by dry flash chromatography (Silica Gel 60H for TLC, 15% EtOAc-hexanes→EtOAc) to afford 0.158 g (81%) the product 8a as a white solid. $^1$H NMR (400 MHz) in CDCl₃+2 drops of CD₃OD (J, Hz): δ 1.53 (3H, d, $^3J$=7.3, α-MeCH), 3.96 (1H, dd, $^2J$=−11.8, $^3J$=2.5, 6-H$_A$), 4.41 (1H, d, $^3J$=4.1, 4-H), 4.44 (1H, dd, $^2J$=−11.8, $^3J$=6.8, 6-H$_B$), 4.55–4.51 (1H, m, 5-H), 5.11 (1H, q, $^3J$=7.3, α-CH), 5.13 (1H, s, CH₂Ph), 7.34–7.24 (5H, m, Ph).

(αR,4R,5R)-2-(α-tert-Butoxycarbonylethyl)-4,5-dihydroxy-1,2-oxazinan-3-one (8b) was obtained as a white solid (mp 93–94° C.) with a yield of 83% from (R)-2-(α-tert-butoxycarbonylethyl)-4,5-dehydro-1,2-oxazinan-3-one (7b) similarly to the preparation of 8a (vide infra) using (DHQ)$_2$PHAL as the asymmetric catalyst. $^1$H NMR (400 MHz) in CDCl$_3$+2 drops of CD$_3$OD (J, Hz): δ 1.44 (3H, d, $^3$J=7.3, α-MeCH), 1.45 (9H, Me$_3$C), 2.25 (2H, br. s, OH, OH), 4.30 (1H, dd, $^2$J=−11.9, $^3$J=2.8, 6-H$_A$), 4.37 (1H, d, $^3$J=4.5, 4-H), 4.38 (1H, dd, $^2$J=−11.9, $^3$J=7.3, 6-H$_B$), 4.56–4.52 (1H, br. m, 5-H), 4.96 (1H, q, $^3$J=7.3, α-CH). $^{13}$C (100 MHz) in CDCl$_3$: δ 13.96, 27.92, 54.89, 68.89, 69.98, 76.55, 83.01, 169.46, 169.94. IR (KBr), cm$^{-1}$: 3423, 2985, 1739, 1662, 1415, 1152. MS (CI, isobutane), m/Z: 261 (M$^+$+1). Anal. Calcd for C$_{11}$H$_{19}$NO$_6$: C, 50.6; H, 7.3; N, 5.4. Found: C, 50.5; H, 7.4; N, 5.4%.

(αR,4S,5S)-2-(α-Carboxyethyl)-4,5-dihydroxy-1,2-oxazinan-3-one (9a). A suspension of 5% Pd-C (0.137 g) in EtOAc (10 mL) was stirred for 1 h under H$_2$ atmosphere and a solution of the benzyl ester 8a (0.137 g, 0.464 mmol) in EtOAc (15 ml) was added portionwise. The reaction mixture was stirred for 8 hours under H$_2$ and filtered through a short pad of Silica Gel 60H (for TLC) followed by washing with MeOH (7×5 mL). After evaporation of the filtrate in vacuo, the residue was triturated with dry ether and dried in vacuo to provide 0.093 g (98%) of the product 9a as a white solid. $^1$H NMR (400 MHz) in CD$_3$CN (J, Hz): δ 1.44 (3H, d, $^3$J=7.3, α-MeCH), 3.00 (2H, br. s, OH, OH), 3.90 (1H, m, 6-H$_A$), 4.37 (1H, d, $^3$J=4.4, 4-H), 4.49–4.43 (2H, m, 6-H$_B$, 5-H), 5.01 (1H, q, $^3$J=7.3, α-CH), 5.31 (1H, br. s, COOH). $^{13}$C (100 MHz) in CD$_3$CN: δ 13.55, 54.34, 70.15, 70.64, 78.41, 171.22, 172.85.

(αR,4R,5R)-2-(α-Carboxyethyl)-4,5-dihydroxy-1,2-oxazinan-3-one (9b). To a cooled (ca. 0° C.) stirred solution of the tert-butyl ester 8b (0.0467 g, 0.179 mmol) in CH$_2$Cl$_2$ (0.9 ml), trifluoroacetic acid (0.9 mL) was added in one portion. The reaction mixture was kept for 1 hour at room temperature and was evaporated in vacuo to dryness. The semisolid residue was triturated with dry ether and dried in vacuo to afford 0.0295 g (80%) of the product 9b as a white solid. $^1$H NMR (400 MHz) in CD$_3$CN (J, Hz): δ 1.41 (3H, d, $^3$J=7.3, α-MeCH), 3.60 (2H, br. s, OH, OH, COOH), 4.14 (1H, dd, $^2$J=−11.6, $^3$J=2.3, 6-H$_A$), 4.34 (1H, d, $^3$J=4.1, 4-H), 4.40 (1H, dd, $^2$J=−11.6, $^3$J=7.4, 6-H$_B$), 4.49–4.45 (2H, m, 5-H), 5.01 (1H, q, $^3$J=7.3, α-CH), 5.31 (1H, br. s, COOH). $^{13}$C (100 MHz) in CD$_3$CN: δ 14.45, 54.48, 70.05, 70.99, 77.77, 167.30, 171.82.

(αR,1R,6R)-2-(α-tert-Butoxycarbonylethyl)-8-thia-3,7,9-trioxa-4-azabicyclo[4.3.0]nona-5,8-dione (10). To a solution of the diol 8b (2.395 g, 9.167 mmol) and Et$_3$N (3.71 g, 36.67 mmol) in dry CH$_2$Cl$_2$ (45 mL), a solution of thionyl chloride (1.64 g, 13.75 mmol) in dry CH$_2$Cl$_2$ (15 mL) was added dropwise with cooling (−15~−20° C.) and stirring. After stirring for 1 hour at −2~2° C., the reaction mixture was diluted with CH$_2$Cl$_2$ (60 mL) and washed with water (20 mL), 1M aqueous citric acid (20 mL), saturated aqueous NaHCO$_3$ (20 mL) and dried over MgSO$_4$. Removal of the solvent provided 2.524 g (90%) of the product 10 (diastereomer ratio is ca. 1:1) as a viscous dark, oil. $^1$H NMR (400 MHz) in CDCl$_3$ (J, Hz): δ 1.45 (9H, Me$_3$C), 1.46 (9H, Me'$_3$C), 1.47 (3H, d, $^3$J=7.3, α-MeCH), 1.49 (3H, d, $^3$J=7.3, α-Me'CH), 4.43 (1H, dd, $^2$J=−12.4, $^3$J=5.5, 2-H$_A$), 4.48(1H, dd, $^2$J=−11.5, $^3$J=5.0, 2-H$_A$'), 4.51 (1H, dd, $^2$J=−11.5, $^3$J=5.0, 2-H$_B$), 4.60 (1H, dd, $^2$J=−12.4, $^3$J=6.5, 2-H$_B$'), 5.01 (1H, q, $^3$J=7.3, α-CH), 5.05 (1H, q, α-CH, $^3$J=7.3), 5.18 (1H, d, $^3$J=8.2, 6-H), 5.22 (1H, m, $^3$J=8.2, 6.5, 5.5, 1-H), 5.37 (1H, d, $^3$J=7.3, 6-H'), 5.50 (1H, m, $^3$J=7.3, 5.0, 1-H'). The compound was used in the next reaction without further purification.

(αR,4S,5R)-2-(α-tert-Butoxycarbonylethyl)-4-azido-5-hydroxy-1,2-oxazinan-3-one (11) To a stirred solution of the cyclic sulfite (2,524 g, 8.21 mmol) in HMPA (15 mL), sodium azide (1.60 g, 24.6 mmol) was added in one portion and the reaction mixture was stirred for 24 hours at room temperature. EtOAc (50 mL) was added and the resultant mixture was washed with water (2×15 ml,) and 1M aqueous citric acid (15 mL). The combined aqueous solutions were extracted with EtOAc (3×15 mL). The combined organic extracts were washed with saturated aqueous NaHCO$_3$ (50 mL), brine (2×50 mL) and dried over MgSO$_4$. After removal of the solvent, the dark oily residue was purified by flash chromatography (Silica Gel 60, 1% MeCN—CH$_2$Cl$_2$→10% MeCN—CH$_2$Cl$_2$) to afford 0.37 g (16%) the product 11 as a yellowish oil. $^1$H NMR (400 MHz) in CDCl$_3$ (J, Hz): δ 1.46 (9H, Me$_3$C), 1.48 (3H, d, $^3$J=7.3, α-MeCH), 2.65 (1H, d, $^3$J=4.5, OH), 4.08–4.02 (1H, m, 5-H), 4.08 (1H, dd, $^2$J=−11.6, $^3$J=3.5, 6-H$_A$), 4.27 (1H, dd, $^2$J=−11.6, $^3$J=6.1, 6-H$_B$), 4.37 (1H, d, $^3$J=7.6, 4-H), 4.93 (1H, q, $^3$J=7.3, α-CH). $^{13}$C (100 MHz) in CDCl$_3$: δ 13.32, 27.98, 55.25, 64.62, 70.52, 75.25, 82.79, 167.33, 168.37. IR (film), cm$^{-1}$: 3436, 2981, 2116, 1739, 1685, 1256, 1158. MS (CI, isobutane), m/Z: 287 (M$^+$+1). Anal. Calcd for C$_{11}$H$_{18}$N$_4$O$_5$: C, 46.2; H, 6.3; N, 19.6. Found: C, 46.4; H, 6.3; N, 19.4%.

(αR,4S,5R)-2-(α-Carboxyethyl)-4-azido-5-hydroxy-1,2-oxazinan-3-one (12). To a cooled (0~−5° C.) stirred solution of the tert-butyl ester 11 (0.469 g, 1.64 mmol) in CH$_2$Cl$_2$ (8 ml), a precooled (ca. 0° C.) trifluoroacetic acid (6.5 mL) was added portionwise. The reaction mixture was kept for 1.5 hours at room temperature and was evaporated in vacuo to dryness. Traces of trifluoroacetic acid were removed by repeated addition and evaporation of dry ether (3×15 mL). After drying in vacuo, 0.373 g (99%) of the product 12 was obtained as a yellowish semisolid. $^1$H NMR (400 MHz) in CDCl$_3$ (J, Hz): δ 1.58 (3H, d, $^3$J=7.4, α-MeCH), 4.10–4.06 (1H, m, 5-H), 4.13 (1H, dd, $^2$J=−11.7, $^3$J=4.1 , 6-H$_A$), 4.31 (1H, dd, $^2$J=−11.7, $^3$J=5.9, 6-H$_B$), 4.43 (1H, d, $^3$J=7.4, 4-H), H), 5.12 (1H, q, $^3$J=7.4, α-CH), 6.51 (2H, br. s, OH, COOH). $^{13}$C (100 MHz) in CD$_3$CN: δ 13.51, 54.74, 65.75, 71.38, 78.21, 167.55, 170.91. IR (film), cm$^{-1}$: 3456, 2959, 2125, 1746, 1654, 1284. MS (CI, isobutane), m/Z: 231 (M$^+$+1). The compound was used in the next reaction without further purification.

(αR,4S,5R)-2-(α-Carboxyethyl)-4-amino-5-hydroxy-1,2-oxazinan-3-one (13). A suspension of 5% Pd—C (0.175 g) in EtOAc (10 mL) was stirred for 1.5 hours under H$_2$ atmosphere and a solution of the azido alcohol 12 (0.373 g, 1.621 mmol) in EtOAc (15 ml) was added portionwise. The reaction mixture was stirred for 17 hours under H$_2$ and was evaporated to dryness. The residue was washed with dry ether (3×15 mL) and the product was extracted from the dried residue with hot (ca. 70° C.) water (30 mL). The aqueous solution was filtered through a paper filter and the black solid was washed with hot water (3×10 mL). Evaporation of the filtrate in vacuo provided 0.296 g (90%) of the product 13 as a white solid with mp 200–202° C. (decomp.). $^1$H NMR (400 MHz) in CD$_3$OD+1 drop of CF$_3$CO$_2$H (J, Hz): δ 1.52 (3H, d, $^3$J=7.4, α-MeCH), 4.08 (1H, dd, $^2$J=−11.7, $^3$J=2.5, 6-H$_A$), 4.18–4.16 (2H, m, 4-H, 5-H), 4.46–4.41 (1H, dd, $^2$J=−11.7, $^3$J=6.4, 6-H$_B$), 4.98 (1H, q, $^3$J=7.4, α-CH). $^{13}$C (100 MHz) in D$_2$O: δ 17.62, 59.62, 61.42, 73.69, 82.48, 169.06, 180.86. IR (KBr), cm$^{-1}$: 3158, 1684, 1599, 1568, 1400. MS (CI, isobutane), m/Z: 205 (M$^+$+1). Anal. Calcd for C$_7$H$_{12}$N$_2$O$_5$+0.5 H$_2$O: C, 39.4; H, 6.1; N, 13.1. Found: C, 39.3; H, 6.2; N, 13.2%.

(αR,4S,5R)-2-(α-Carboxyethyl)-4-phenylacetylamino-5-hydroxy-1,2-oxazinan-3-one (14). To a solution of the amino acid 13 (0.290 g, 1.36 mmol) and NaHCO$_3$ (0.343 g, 4.08 mmol) in water (7 mL), a solution of phenylacetyl chloride (0.191 g, 1.24 mmol) in abs. MeCN (3 mL) was added dropwise with cooling (−5∼−6° C.) and stirring. The reaction mixture was stirred for 2 h at 0∼−2° C. and for 1 hour at room temperature and was concentrated in vacuo to a volume of circa 5 mL. The solution was cooled to ca. 5° C. and adjusted to pH 2–3 with 1M aqueous HCl. (2.8 mL). The white precipitate was filtered off, washed with water and dried in vacuo to afford 0.364 g (91%) of the product 14 as a white solid with mp 194–195° C. (decomp.) (from iso-PrOH). $^1$H NMR (400 MHz) in CD$_3$OD (J, Hz): δ 1.47 (3H, d, $^3$J=7.3, α-MeCH), 3.62 (1H, d, $^2$J=−14.8, CH$_A$Ph), 3.67 (1H, d, $^2$J=−14.8, CH$_B$Ph), 4.06 (1H, dd, $^2$J=−11.4, $^3$J=3.7, 6-H$_A$), 4.12–4.06 (1H, m, 5-H), 4.33 (1H, dd, $^2$J=−11.4, $^3$J=5.6, 6-H$_B$), 4.66 (1H, d, $^3$J=8.0, 4-H), 4.96 (1H, q, $^3$J=7.3, α-CH), 7.38–7.17 (5H, m, Ph). $^{13}$C (100 MHz) in CD$_3$OD: δ 1371, 43.63, 55.70, 57.54, 71.84, 79.10, 127.85, 129.51, 130.37, 136.63, 169.61, 172.71, 174.89. IR (KBr), cm$^{-1}$: 3361, 2913, 1729, 1666, 1630, 1542, 1440, 1233. MS (CI, isobutane), m/Z: 323 (M$^+$+1). Anal. Calcd for C$_{15}$H$_{18}$N$_2$O$_6$: C, 55.9; H, 5.6; N, 8.7. Found: C, 55.7; H, 5.7; N, 8.6%.

Example 4

Bioassay of Oxazinones

Samples of 2-carboxymethyl-5-hydroxy-1,2-oxazin-3-one and penicillin were applied to a filter disc in the amounts indicated in Table 1, below. The discs were applied to agar plates seeded with *Micrococcus luteus*, and the plates were incubated over night at 37° C. The results are summarized in the following Table 1:

TABLE 1

| Compound | Weight (micrograms) | Zone Size (cm) |
|---|---|---|
| Water Blank | | 0 |
| Penicillin G | 0.1 | 1.6 |
| 2-carboxymethyl-5-hydroxy-1,2-oxazin-3-one | 100 | 1.1 |
| 2-carboxymethyl-5-hydroxy-1,2-oxazin-3-one | 1000 | 2.0 |

Samples of 2-[2-carboxypropyl]-5-hydroxy-1,2-oxazin-3-one and desacetoxycephalosporin G were applied to a filter disc in the amounts indicated in Table 2, below. The discs were applied to agar plates seeded with *Micrococcus luteus*, and the plates were incubated overnight at 37° C. The results are summarized in the following Table 2:

TABLE 2

| Compound | Weight (micrograms) | Zone Size (cm) |
|---|---|---|
| Water Blank | | 0 |
| desacetoxycephalosporin G | 2.5 | 2.5 |
| 2-[2-carboxypropyl]-5-hydroxy-1,2-oxazin-3-one | 12.0 | 2.0 |

With reference to Tables 1 and 2, the bioassays suggest that 2-carboxymethyl-5-hydroxy-1,2-oxazin-3-one exhibits weak antibacterial activity at least 1000 times less than that of penicillin. In contrast, 2-[2-carboxypropyl]-5-hydroxy-1,2-oxazin-3-one has approximately 50 times the activity of 2-carboxymethyl-5-hydroxy-1,2-oxazin-3-one.

Equivalents

Those skilled in the art will recognize, or be able to ascertain using no more than routine experimentation, many equivalents to the specific embodiments and methods described herein. Such equivalents are intended to be encompassed by the scope of the following claims.

All patents, patent applications, and literature references cited herein are hereby expressly incorporated by reference.

What is claimed is:

1. A compound of formula (I):

(I)

wherein:
   R$_1$ is an amino acid side chain mimicking moiety;
   R$_4$, R$_6$, R$_8$, and R$_9$ are substituting moieties;
   R$_7$ is hydrogen, a protecting moiety, or a prodrug, or an acceptable salt, or an ester thereof.

2. The compound of formula (I) of claim 1, wherein R$_1$ is a side chain of an amino acid.

3. The compound of formula (I) of claim 2, wherein R$_1$ is selected from the group consisting of the side chains of alanine, valine, leucine, isoleucine, phenylalanine, tryptophan, and methionine.

4. The compound of formula (I) of claim 2, wherein R$_1$ is selected from the group consisting of the side chains of glycine, serine, threonine, cysteine, tyrosine, asparagine, and glutamine.

5. The compound of formula (I) of claim 2, wherein R$_1$ is selected from the group consisting of the side chains of aspartic acid, glutamic acid, lysine, arginine, and histidine.

6. The compound of formula (I) of claim 3, wherein R$_1$ is the side chain of alanine.

7. The compound of formula (I) of claim 1, wherein R$_1$ is alkyl.

8. The compound of formula (I) of claim 7, wherein said alkyl is lower alkyl.

9. The compound of formula (I) of claim 8, wherein said alkyl is methyl, ethyl, i-propyl, n-propyl, i-butyl, n-butyl, t-butyl, pentyl, or hexyl.

10. The compound of formula (I) of claim 9, wherein said alkyl is substituted with one or more substituents.

11. The compound of formula (I) of claim 1, wherein R$_1$ is alkenyl, alkynyl, carbonyl, aralkyl or aryl.

12. The compound of formula (I) of claim 11, wherein R$_1$ is aryl.

13. The compound of formula (I) of claim 12, wherein R$_1$ is substituted or unsubstituted phenyl.

14. The compound of formula (I) of claim 1, wherein the * carbon has an S configuration.

15. The compound of formula (I) of claim 1, wherein the * carbon has an R configuration.

16. The compound of formula (I) of claim 1, wherein R$_7$ is hydrogen.

17. The compound of formula (I) of claim 1, wherein R$_4$ is hydrogen or lower alkyl.

18. The compound of formula (I) of claim 1, wherein R$_6$ is hydrogen or lower alkyl.

19. The compound of formula (I) of claim 1, wherein R$_8$ is hydrogen.

20. The compound of formula (I) of claim 1, wherein R$_9$ is hydrogen.

21. A method for synthesizing a compound of the formula (II):

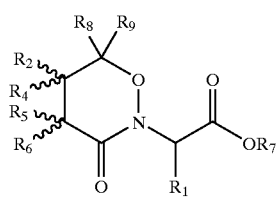

(II)

wherein:

R₁ is an amino acid side chain mimicking moiety;

R₂ is halogen, OH, SH, NH₂, NHCOR₃, or an electronegative moiety;

R₃ is an antibacterial substituent;

R₄, R₈ and R₉ are each independently selected substituting moieties;

R₅ is OH, NH₂, NHCOR₃, or an electronegative moiety; and

R₆ is a substituting moiety or the oxygen of a carbonyl group when taken together with R₅;

R₇ is hydrogen, a protecting moiety, or a prodrug, or a pharmaceutically acceptable salt, or an ester thereof, comprising:

contacting a compound of formula (I) with a derivatizing agent, under appropriate conditions such that compound of formula (II) is synthesized, wherein said compound of formula (I) is:

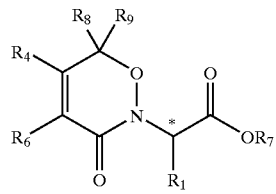

(I)

wherein:

R₁ is an amino acid side chain mimicking moiety;

R₄, R₆, R₈ and R₉ are each independently selected substituting moieties;

R₇ is hydrogen, a protecting group, or a prodrug moiety, and pharmaceutically acceptable salt, or ester thereof.

22. The method of claim 21, wherein said compound of formula (II) has the following stereochemistry:

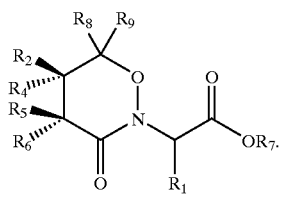

23. The method of claim 21, wherein said compound of formula (II) has the following stereochemistry:

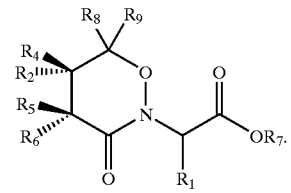

24. The method of claim 21, wherein said compound of formula (II) has the following stereochemistry:

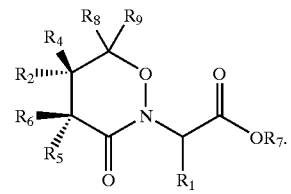

25. The method of claim 21, wherein said compound of formula (II) has the following stereochemistry:

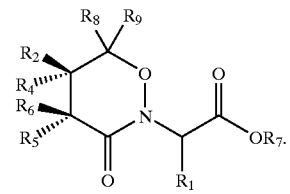

26. The method of claim 21, further comprising the formation of an epoxide oxazinone intermediate.

27. The method of claim 22, wherein said epoxide oxazinone intermediate is formed stereoselectively.

28. The method of claim 22 or 23, wherein said compound of formula (II) is formed from said epoxide oxazinone intermediate by contacting said epoxide oxazinone with a epoxide opening agent.

29. The method of claim 21, wherein said derivatizing agent selectively aminohydroxylates said compound of formula (I).

30. The method of claim 21, wherein said derivatizing agent selectively dihydroxylates said compound of formula (I).

31. The method of claim 21, wherein said derivatizing agent selectively halogenates said compound of formula (I).

32. The method of claim 31, wherein said halogenation is a fluorination.

33. A compound of formula (III):

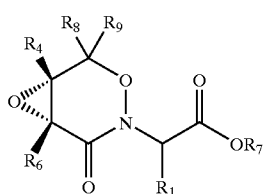

(III)

wherein:

R₁ is an amino acid side chain mimicking moiety;

R₄, R₆, R₈, and R₉ are each independently selected substituting moieties;

R₇ is hydrogen, a protecting moiety, or a prodrug moiety, or an acceptable salt, or ester thereof.

34. A compound of formula (IV):

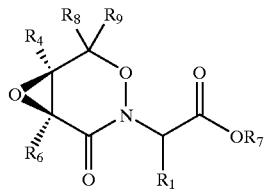

(IV)

wherein:

$R_1$ is an amino acid side chain mimicking moiety;

$R_4$, $R_6$, $R_8$, and $R_9$ are each independently selected substituting moieties;

$R_7$ is hydrogen, a protecting moiety, or a prodrug moiety, or an acceptable salt, or an ester thereof.

35. A method for the synthesis of a compound of formula (I) comprising:

contacting a diolefin with a cyclization catalyst under appropriate conditions, such that a compound of formula (I) is formed, wherein said diolefin is of formula (V):

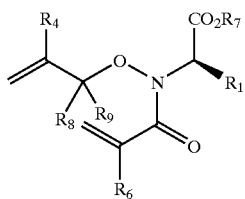

(V)

and wherein said compound of the formula (I) is:

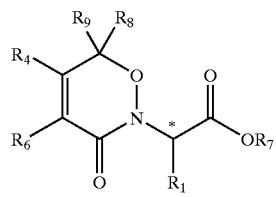

(I)

wherein:

$R_1$ is an amino acid side chain mimicking moiety;

$R_4$, $R_6$, $R_8$, and $R_9$ are substituting moieties;

$R_7$ is hydrogen, a protecting moiety, or a prodrug moiety, and, or an acceptable salt, or an ester thereof.

36. The method of claim 35, wherein said cyclization catalyst is bis(tricyclohexylphosphine) benzylidene ruthenium dichloride.

37. The method of claim 35, wherein said appropriate conditions comprise a non-polar solvent.

38. The method of claim 37, wherein said non-polar solvent is methylene chloride or benzene.

39. A method for the synthesis of a compound of formula (I) comprising:

treating an olefinic triphenyl phosphine salt with ozone under appropriate conditions, such that a compound of formula (I) is formed, wherein said olefinic triphenyl phosphine salt is of formula (VI)

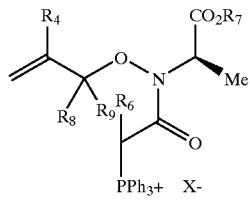

(VI)

and wherein said compound of formula (I) is:

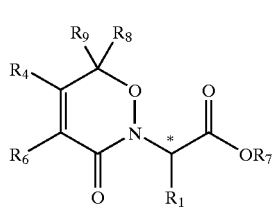

(I)

wherein:

$R_1$ is an amino acid side chain mimicking moiety;

$R_4$, $R_6$, $R_8$, and $R_9$ are substituting moieties;

$R_7$ is hydrogen, a protecting moiety, or a prodrug moiety, or an acceptable salt, or an ester thereof.

40. The method of claim 39, wherein said olefinic triphenyl phosphine salt is a triflic acid salt.

41. A method for treating a bacterial associated state in a subject, comprising administering to said subject an effective amount of a compound of formula (I), such that the subject is treated for said bacterial associated state, and wherein said compound of formula (I) is:

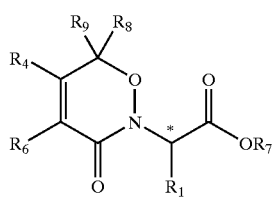

(I)

wherein:

$R_1$ is an amino acid side chain mimicking moiety;

$R_4$, $R_6$, $R_8$, and $R_9$ are substituting moieties;

$R_7$ is hydrogen, a protecting moiety, or a prodrug moiety, or an acceptable salt, or an ester thereof.

42. A method for treating a bacterial associated state in a subject, comprising administering to said subject an effective amount of compound of formula (III), such that the subject is treated for said bacterial associated state, and wherein said compound of formula (III) is:

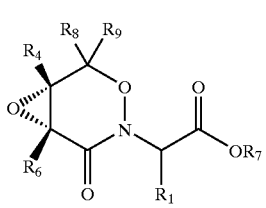

(III)

wherein:
R₁ is an amino acid side chain mimicking moiety;
R₄, R₆, R₈, and R₉ are each independently selected substituting moieties;
R₇ is hydrogen, a protecting moiety, or a prodrug moiety, or an acceptable salt, or an ester thereof.

43. A method for treating a bacterial associated state in a subject, comprising administering to said subject an effective amount of a compound of formula (IV), such that the subject is treated for said bacterial associated state, and wherein said compound of formula (IV) is:

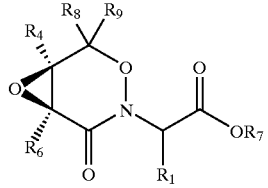

(IV)

wherein:

R₁ is an amino acid side chain mimicking moiety;

R₄, R₆, R₈, and R₉ are each independently selected substituting moieties;

R₇ is hydrogen, a protecting moiety, or a prodrug moiety, or an acceptable salt, or an ester thereof.

44. A pharmaceutical composition, comprising a therapeutically effective amount of a compound of any one of the claims 1, 33, or 34 and a pharmaceutically acceptable carrier.

45. The pharmaceutical composition of claim 44, wherein said therapeutically effective amount is effective to treat a bacterial associated state in a subject.

* * * * *